US006987104B2

(12) United States Patent
Jacobs et al.

(10) Patent No.: US 6,987,104 B2
(45) Date of Patent: Jan. 17, 2006

(54) PYRROLIDINE BICYCLIC COMPOUNDS AND ITS DERIVATIVES, COMPOSITIONS AND METHODS OF USE

(75) Inventors: Jeffrey Jacobs, San Mateo, CA (US); Rakesh K. Jain, Fremont, CA (US); Jason G. Lewis, Hayward, CA (US); Dinesh V. Patel, Fremont, CA (US); Zhengyu Yuan, Fremont, CA (US)

(73) Assignee: Vicuron Pharmaceuticals Inc., Fremont, CA (US)

(*) Notice: Subject to any disclaimer, the term of this patent is extended or adjusted under 35 U.S.C. 154(b) by 406 days.

(21) Appl. No.: 10/171,705

(22) Filed: Jun. 14, 2002

(65) Prior Publication Data

US 2003/0069223 A1 Apr. 10, 2003

Related U.S. Application Data

(60) Provisional application No. 60/298,418, filed on Jun. 15, 2001.

(51) Int. Cl.
*A01N 43/46* (2006.01)
*C07D 403/12* (2006.01)
*A61K 31/55* (2006.01)

(52) U.S. Cl. ............... 514/215; 548/530; 548/201; 548/123; 548/124; 548/127; 548/128; 548/131; 548/200; 548/135; 548/136; 548/143; 548/182; 548/206; 548/215; 548/262.2; 548/300.1; 548/311.1; 548/356.1; 548/364; 548/366.4; 548/363; 548/326; 548/360; 548/373; 548/378; 548/401; 548/596; 548/208

(58) Field of Classification Search ................. 514/215; 548/530, 201, 123, 128, 131, 200, 136, 143, 548/182, 262.2, 300, 373, 596
See application file for complete search history.

(56) References Cited

U.S. PATENT DOCUMENTS

| | | | | |
|---|---|---|---|---|
| 4,052,511 A | | 10/1977 | Cushman et al. ........... 424/274 |
| 4,290,952 A | * | 9/1981 | Freed et al. ............... 548/533 |
| 4,303,662 A | | 12/1981 | Sprague ..................... 424/256 |
| 4,311,705 A | | 1/1982 | Ondetti et al. ............. 424/274 |
| 4,320,057 A | * | 3/1982 | Freed et al. ............... 540/490 |
| 4,321,383 A | | 3/1982 | Sprague ..................... 546/113 |
| 4,599,361 A | | 7/1986 | Dickens et al. ............ 514/575 |
| 4,804,676 A | | 2/1989 | Inaoka et al. .............. 514/423 |
| 5,128,346 A | | 7/1992 | Nadzan et al. ............. 514/307 |
| 5,256,657 A | | 10/1993 | Singh et al. .............. 514/228.2 |
| 5,268,384 A | | 12/1993 | Galardy ..................... 514/419 |
| 5,447,929 A | | 9/1995 | Broadhurst et al. ....... 514/228.2 |
| 5,453,423 A | | 9/1995 | Long et al. ................. 514/211 |
| 5,552,419 A | | 9/1996 | MacPherson et al. ....... 514/357 |
| 5,614,625 A | | 3/1997 | Broadhurst et al. ......... 540/480 |
| 5,643,908 A | | 7/1997 | Sugimura et al. ........... 514/247 |
| 5,712,300 A | | 1/1998 | Jacobsen ..................... 514/389 |
| 5,869,518 A | | 2/1999 | Bedoya Zurita et al. .... 514/412 |
| 5,876,727 A | * | 3/1999 | Swain et al. ............. 424/193.1 |

FOREIGN PATENT DOCUMENTS

| | | |
|---|---|---|
| EP | 236 872 | 9/1987 |
| EP | 274 453 | 7/1988 |
| EP | 334 244 | 9/1989 |
| EP | 423 943 | 4/1991 |
| EP | 489 577 | 6/1992 |
| EP | 489 579 | 6/1992 |
| EP | 497 192 | 8/1992 |
| EP | 574 758 | 12/1993 |
| WO | WO 90/05716 | 5/1990 |
| WO | WO 90/05719 | 5/1990 |
| WO | WO 91/02716 | 3/1991 |
| WO | WO 92/13831 | 8/1992 |
| WO | WO 92/22523 | 12/1992 |
| WO | WO 93/09090 | 5/1993 |
| WO | WO 93/09097 | 5/1993 |
| WO | WO 93/20047 | 10/1993 |
| WO | WO 93/24449 | 12/1993 |
| WO | WO 93/24475 | 12/1993 |
| WO | WO 94/02446 | 2/1994 |
| WO | WO 94/02447 | 2/1994 |
| WO | WO 94/21612 | 9/1994 |
| WO | WO 94/25434 | 11/1994 |
| WO | WO 94/25435 | 11/1994 |
| WO | WO 95/33731 | 12/1995 |
| WO | WO 96/25156 | 8/1996 |
| WO | WO 96/26918 | 9/1996 |
| WO | WO 97/30707 | 8/1997 |
| WO | WO 97/49674 | 12/1997 |
| WO | WO 98/55449 | 12/1998 |
| WO | WO 99/02510 | 1/1999 |
| WO | WO 99/39704 | 8/1999 |
| WO | WO 01/44178 | 6/2001 |
| WO | WO 02/28829 | 4/2002 |

OTHER PUBLICATIONS

Bord et al., "Stromelysin–1 (MMP–3) and Stromelysin–2 (MMP–10) Expression in Developing Human Bone: Potential Roles in Skeletal Development", Bone, vol. 23, No. 1, pp. 7–12 (1998).

Chang et al., "Methionine Aminopeptidase Gene of *Escherichia coli* Is Essential for Cell Growth", J. Bacteriol., vol. 171, No. 7, pp. 4071–4072 (1989).

(Continued)

*Primary Examiner*—James O. Wilson
*Assistant Examiner*—Paul V Ward
(74) *Attorney, Agent, or Firm*—Thomas R. Savitsky

(57) ABSTRACT

N-[1-oxo-(optionally 2-aza)-2-alkyl-3-(carboxyl or thiol or hydroxyaminocarbonyl or N-hydroxyformamido)-propyl]-(aryl or heteroaryl)-azacyclo$_{4-7}$alkanes or thiazacyclo$_{4-7}$alkanes, salts or prodrugs thereof have interesting properties, e.g., in the treatment or prevention of disorders amenable to treatment by PDF inhibitors, such as treatment of bacterial infections.

36 Claims, No Drawings

OTHER PUBLICATIONS

Durand et al., "Peptide Aldehyde Inhibitors of Bacterial Peptide Deformylases", Arch. Biochem. Biophys., vol. 367, No. 2, pp. 297–302 (1999).

Gearing et al., "Processing of Tumour Necrosis Factor–α Precursor by Metalloproteinasis", Nature, vol. 370, pp. 555–557 (1994).

Hao et al., "Structural Basis for the Design of Antibiotics Targeting Peptide Deformylase", Biochemistry, vol. 38, No. 15, pp. 4712–4719 (1999).

Hu et al., "H–Phosphonate Derivatives as Novel Peptide Deformylase Inhibitors", Bioorg. Med. Chem. Letts., vol. 8, pp. 2479–2482 (1998).

Izquierdo–Martin et al., "Mechanistic Studies on the Inhibition of Thermolysin by a Peptide Hydroxamic Acid", J. Am. Chem. Soc., vol. 114, No. 1, pp. 325–331 (1992).

Liu et al., "Distinct Expression of Gelatinase A [Matrix Metalloproteinase (MMP)–2], Collagenase–3 (MMP–13), Membrane Type MMP 1 (MMP–14), and Tissue Inhibitor of MMPs Type 1 Mediated by Physiological Signals During Formation and Regression of the Rat Corpus Luteum", Endocrinology, vol. 140, No. 11, pp. 5330–5338 (1999).

Mazel et al., Genetic Characterization of Polypeptide Deformylase, a Distinctive Enzyme of Eubacterial Translation, EMBO J., vol. 13, No. 4, pp. 914–923.

McGeehan et al., "Regulation of Tumour Necrosis Factor–a Processing by a Metalloproteinase Inhibitor", Nature, vol. 370, pp. 558–561 (1994).

Meinnel et al., "Characterization of the Thermus thermophilus Locus Encoding Peptide Deformylase and Methionyl–tRNA$_1^{Met}$ Formyltransferase", J. Bacteriol., vol. 176, No. 23, pp. 7387–7390 (1994).

Meinnel et al., "Structure–Function Relationships within the Peptide Deformylase Family. Evidence for a Conserved Architecture of the Active Site Involving Three Conserved Motifs and a Metal Ion", J. Mol. Biol., vol. 267, pp. 749–761 (1997).

Meinnel et al., "Design and Synthesis of Substrate Analogue Inhibitors of Peptide Deformylase", Biochemistry, vol. 38, No. 14, pp. 4287–4295 (1999).

Mohler et al., "Protection Against a Lethal Dose of Endotoxin by an Inhibitor of Tumour Necrosis Factor Processing", Nature, vol. 370, pp. 218–220 (1994).

O'Connell et al., "A High Quality Nuclear Magnetic Resonance Solution Structure of Peptide Deformylase from Escherichia coli: Application of an Automated Assignment Strategy Using GARANT", J. Biomol. NMR, vol. 13, No. 4, pp. 311–324 (1999).

Rajagopalan et al., "Purification, Characterization, and Inhibition of Peptide Deformylase from Escherichia coli", Biochemistry, vol. 36, No. 45, pp. 13910–13918 (1997).

Yamagiwa et al., "Expression of Metalloproteinase–13 (Collagenase–3) Is Induced During Fracture Healing in Mice", Bone, vol. 25, No. 2, pp. 197–203 (1999).

* cited by examiner

PYRROLIDINE BICYCLIC COMPOUNDS AND ITS DERIVATIVES, COMPOSITIONS AND METHODS OF USE

FIELD OF INVENTION

This invention is directed to novel pyrrolidine bicyclic compounds, their uses as pharmaceuticals and pharmaceutical compositions comprising them.

BACKGROUND OF THE INVENTION

Treatment of microbial infection in host organisms requires an effective means to kill the microbe while doing as little harm to the host as possible. Accordingly, agents which target characteristics unique to a pathology-causing microorganism are desirable for treatment. Penicillin is an extremely well-known example of such an agent. Penicillin acts by inhibiting biosynthesis of bacterial cell walls. Since mammalian cells do not require cell walls for survival, administration of penicillin to a human infected with bacteria may kill the bacteria without killing human cells.

However, the use of antibiotics and antimicrobials has also resulted in increased resistance to these agents. As bacteria become resistant to older, more widely used antimicrobial agents, new antimicrobials must be developed in order to provide effective treatments for human and non-human animals suffering from microbial infection.

Peptidyl deformylase (PDF) is a metallopeptidase found in prokaryotic organisms, such as bacteria. Protein synthesis in prokaryotic organisms begins with N-formyl methionine (fMet). After initiation of protein synthesis, the formyl group is removed by the enzyme PDF; this activity is essential for maturation of proteins. It has been shown that PDF is required for bacterial growth (see Chang et al., J. Bacteriol., Vol.171, pp. 4071–4072 (1989); Meinnel et al., J. Bacteriol., Vol.176, No. 23, pp.7387–7390 (1994); Mazel et al., *EMBO J.*, Vol. 13, No. 4, pp. 914–923 (1994)). Since protein synthesis in eukaryotic organisms does not depend on fMet for initiation, agents that will inhibit PDF are attractive candidates for development of new antimicrobial and antibacterial drugs. Prokaryotic organisms, including disease-causing prokaryotes, are described in Balows, Truper, Dworkin, Harder and Schleifer, Eds., The Prokaryotes, 2$^{nd}$ Ed., Springer-Verlag, NY (1992); and Holt, Editor-in-Chief, Bergey's Manual of Systematic Bacteriology, Vols. 1–4, Williams & Wilkins, Baltimore (1982, 1986, 1989).

PDF is part of the metalloproteinase superfamily. While PDF clearly shares many of the features which characterize metalloproteinases, it differs from other members of the superfamily in several important respects. First, the metal ion in the active enzyme appears to be Fe (II), or possibly another divalent cationic metal, instead of the zinc ion more commonly encountered (see Rajagopalan et al., J. Am. Chem. Soc., Vol. 119, pp. 12418–12419 (1997)). Second, the divalent ion appears to play an important role, not only in catalysis, but also in the structural integrity of the protein. Third, the third ligand of the divalent ion is a cysteine, rather than a histidine or a glutamate, as in other metalloproteinases and is not located at the C-terminal side of the HEXXH motif but far away along the amino acid sequence and N-terminal to the motif. Finally, the solution structure shows significant differences in the secondary and tertiary structure of PDF compared to other prototypical metalloproteinases (see Meinnel et al., J. Mol. Biol., Vol. 262, pp. 375–386 (1996)). PDF from *E. coli, Bacillus stearothermophilus* and *Thermus thermophilus* have been characterized (see Meinnel et al., J. Mol. Biol., Vol. 267, pp. 749–761 (1997)). The enzyme studied by Meinnel et al. contained a zinc ion as the divalent ion and the structural features summarized above were obtained from zinc-containing proteins. The structure of the protein has also been determined by NMR (see O'Connell et al., *J. Biomol., NMR*, Vol. 13, No. 4, pp. 311–324 (1999)).

Metalloproteinases are critical to many aspects of normal metabolism. The class known as matrix metalloproteinases (MMPs) are involved in tissue remodeling, such as degradation of the extracellular matrix. These enzymes are believed to play a role in normal or beneficial biological events, such as the formation of the corpus luteum during pregnancy (see Liu et al., *Endocrinology*, Vol. 140, No. 11, pp. 5330–5338 (1999)), wound healing (see Yamagiwa et al., *Bone*, Vol. 25, No. 2, pp. 197–203 (1999)), and bone growth in healthy children (see Bord et al., *Bone*, Vol. 23, No. 1, pp. 7–12 (1998)). Disorders involving metalloproteinases have been implicated in several diseases such as cancer, arthritis and autoimmune diseases.

Because of the importance of MMPs in normal physiological processes, it would be preferable to develop agents that inhibit PDF, a metalloproteinase present only in prokaryotes, while avoiding significant inhibition of MMPs. Alternatively, PDF inhibitors which also inhibit MMPs may be of use where the therapeutic benefits of inhibiting PDF outweigh the risk of side effects from MMP inhibition.

A wide variety of compounds have been developed as candidate inhibitors of MMPs and other metalloproteinases, and much effort has also been directed at synthetic methods for these compounds and related compounds (see Izquierdo-Martin et al., J. Am. Chem. Soc., Vol. 114, pp. 325–331 (1992); Cushman et al., Chapter 5, "Specific Inhibitors of Zinc Metallopeptidases", Topics in Molecular Pharmacology, Burgen & Roberts, Eds. (1981); Mohler et al., Nature, Vol. 370, pp. 218–220 (1994); Gearing et al., Nature, Vol. 370, pp. 555–557 (1994); McGeehan et al., Nature, Vol. 370, pp. 558–561 (1994); U.S. Pat. Nos. 4,052, 511, 4,303,662, 4,311,705, 4,321,383, 4,599,361, 4,804,676, 5,128,346, 5,256,657, 5,268,384, 5,447,929, 5,453,423, 5,552,419, 5,614,625, 5,643,908, 5,712,300 and 5,869,518; European patent publications EP 236872, EP 274453, EP 334244, EP 423943, EP 489577, EP 489579, EP 497192, EP 574758; and International PCT Patent Applications Publication Nos. WO 90/05716, WO 90/05719, WO 91/02716, WO 92/13831, WO 92/22523, WO 93/09090, WO 93/09097, WO 93/20047, WO 93/24449, WO 93/24475, WO 94/02446, WO 94/02447, WO 94/21612, WO 94/25434, WO 94/25435, WO 95/33731, WO 96/25156, WO 96/26918 WO 97/30707, WO 97/49674, WO 98/55449 and WO 99/02510.

Research on inhibitors of PDF is much less extensive than that for inhibitors of MMPs. N-formyl hydroxylamine derivatives are described in International Patent Application WO 99/39704. Peptide aldehyde inhibitors of PDFs are described in Durand et al., Arch. Biochem. Biophys., Vol. 367, No. 2, pp. 297–302 (1999). The PDF inhibitor (S)-2-O-(H-phosphonoxy)-L-caproyl-L-leucyl-p-nitroanilide is described in Hao et al., Biochem., Vol. 38, pp. 4712–4719 (1999), and peptidyl H-phosphonate inhibitors of PDF are discussed in Hu et al., Bioorg. Med. Chem. Lett., Vol. 8, pp. 2479–2482 (1998). Formylated peptides and pseudopeptides are described in Meinnel et al., Biochem., Vol. 38, No. 1, pp. 4288–4295 (1999) as inhibitors of PDF.

In view of the importance of identifying new antibiotics to treat bacteria resistant to existing antibiotics, and the relatively small amount of work that has been carried out on PDF inhibitors, it is desirable to develop novel inhibitors of PDF for evaluation and use as antibacterial and antimicrobial agents. The present invention fulfills this need.

SUMMARY OF THE INVENTION

In particular, the present invention provides an N-[1-oxo-(optionally 2-aza)-2-alkyl-3-(carboxyl or thiol or hydroxyaminocarbonyl or N-hydroxyformamido)-propyl]-(aryl or heteroaryl)-azacyclo$_{4-7}$alkane or thiazacyclo$_{4-7}$alkane (referred to herein collectively as "compounds of the invention"), a salt thereof or a prodrug thereof, e.g., a compound of formula (I):

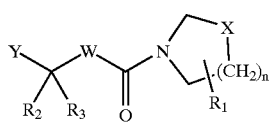

wherein

R$_1$ is aryl or heteroaryl which is linked to either the α-or β-position to the ring nitrogen;

R$_2$ is hydrogen, halogen or hydroxy;

R$_3$ is hydrogen, halogen, C$_{1-10}$alkyl, C$_{1-10}$heteroalkyl or (R$_2$ and R$_3$) collectively form a C$_{4-7}$cycloalkyl, provided that when R$_3$ is halogen, R$_2$ is not hydroxy;

X is —CH$_2$— or S;

W is NR$_5$ or CR$_4$R$_5$, wherein R$_4$ is hydrogen, halogen, C$_{1-10}$alkyl, or C$_{1-10}$heteroalkyl and R$_5$ is C$_{1-10}$alkyl or (R$_4$ and R$_5$) collectively form a C$_{4-7}$cycloalkyl, provided that when W is NR$_5$, R$_2$ and R$_3$ are hydrogen, C$_{1-10}$alkyl or heteroalkyl;

Y is —COOH, —SH, —N(OH)—CHO or —CO—NH(OH), provided that when Y is —N(OH)CHO or —SH, R$_2$ is hydrogen and R$_3$ is hydrogen, C$_{1-10}$alkyl or C$_{1-10}$heteroalkyl;

n is 0 to 3, provided that when n is 0, X is —CH$_2$—; a salt thereof or a prodrug therof.

DETAILED DESCRIPTION OF THE INVENTION

Unless otherwise stated, the following terms as used in the specification have the following meaning.

The term "cycloalkane" or "cycloalkyl" is a cyclic saturated alkyl group containing from 3- to 6-ring carbon atoms, and is, e.g., cyclopropyl, cyclobutyl, cyclopentyl and cyclohexyl.

The term "azacyclo$_{4-7}$alkane" contains 1-ring heteroatom which is a nitrogen. It contains from 4–7, and preferably 5-ring atoms including the heteroatom.

The term "thiazacyclo$_{4-7}$alkane" contains 2-ring heteroatoms, nitrogen and sulfur. It contains from 4–7, and especially 5-ring atoms including the heteroatom.

The azacyclo$_{4-7}$alkane and thiazacycio$_{4-7}$alkane are substituted at either the α- or β-position to the nitrogen of the ring by a heteroaryl or aryl as defined below.

The term "alkyl" refers to saturated and unsaturated aliphatic groups, cycloalkyl or substituted alkyl including straight-chain, branched-chain and cyclic groups having from 1–10 carbons atoms, and is preferably a saturated lower alkyl having from 1–7 carbon atoms, and especially 1–4 carbon atoms. Examples of alkyl include, but are not limited to, methyl, ethyl, n-propyl, isopropyl, n-butyl, isobutyl, sec-butyl, t-butyl, n-pentyl, neopentyl, n-hexyl or n-heptyl, cyclopropyl and especially n-butyl.

The term "substituted alkyl" refers to an alkyl group that is substituted with one or more substitutents preferably 1–3 substitutents including, but not limited to substituents, such as halogen, lower alkoxy, hydroxy, mercapto, carboxy, cycloalkyl, aryl, heteroaryl and the like. Examples of substituted alkyl groups include, but are not limited to, —CF$_3$, —CF$_2$—CF$_3$, hydroxymethyl, 1- or 2-hydroxyethyl, methoxymethyl, 1- or 2-ethoxyethyl, carboxymethyl, 1-or 2-carboxyethyl, cyclopentylethyl and the like.

The term "aryl" or "Ar" refers to an aromatic carbocyclic group of 6–14 carbon atoms having a single ring including, but not limited to, groups, such as phenyl; or multiple condensed rings including, but not limited to, groups, such as naphthyl or anthryl; and is especially phenyl. An aryl group can be unsubstituted or substituted with one or more substituents, preferably 1–3 substituents including, but not limited to, groups, such as lower alkyl, halogen and lower alkoxy.

The term "heteroaryl" or "HetAr" refers to a 4- to 7-membered, monocyclic aromatic heterocycle or a bicycle that is composed of a 4- to 7-membered, monocyclic aromatic heterocycle and a fused-on benzene ring. The heteroaryl has at least one hetero atom, preferably one or two heteroatoms including, but not limited to, heteroatoms, such as N, O and S, within the ring. Representative examples include, but are not limited to, oxazolyl, thiazolyl, pyridinyl and imidazolyl, benzimidazolyl, isoxazolyl, benzthiazolyl and the like. The heteroaryl may be unsubstituted or substituted by one or more substituents including, but not limited to lower alkyl, halo-lower alkyl, halogen, hydroxy, lower alkoxy, aryl (preferably aryl) and the like.

The term "heteroalkyl" refers to a saturated or unsaturated alkyl as defined above, having from 1–10 carbon atoms, and especially a saturated lower heteroalkyl of 1–4 carbon atoms which contain one or more heteroatoms, as part of the main, branched or cyclic chains in the group. Heteroatoms are independently selected from the group consisting of —NR— where R is hydrogen or alkyl, —S—, —O— and —P—; preferably —NR— where R is hydrogen or alkyl and/or —O—. Heteroalkyl groups may be attached to the remainder of the molecule either at a heteroatom (if a valence is available) or at a carbon atom. Examples of heteroalkyl groups include, but are not limited to, groups, such as —O—CH$_3$, —CH$_2$—O—CH$_3$, —CH$_2$—CH$_2$—O—CH$_3$, —S—CH$_2$—CH$_2$—CH$_3$, —CH$_2$—CH(CH$_3$)—S—CH$_3$ and —CH$_2$—CH$_2$—NH—CH$_2$—CH$_2$—.

The heteroalkyl group may be unsubstituted or substituted with one or more substituents, preferably 1–3 substituents including, but not limited to, alkyl, halogen, alkoxy, hydroxyl, mercapto, carboxy and phenyl. The heteroatom(s) as well as the carbon atoms of the group may be substituted. The heteroatom(s) may also be in oxidized form.

The term "alkoxy" as used herein refers to a C$_{1-10}$alkyl linked to an oxygen atom, or preferably a saturated lower alkoxy having from 1–7 carbon atoms. Examples of alkoxy groups include, but are not limited to, groups, such as methoxy, ethoxy, tert-butoxy and allyloxy.

The term "halogen" or "halo" as used herein refer to chlorine, bromine, fluorine, iodine, and is especially fluorine.

"Protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups may be found in Greene et al., Protective Groups in Organic Synthesis, 2$^{nd}$ Ed., John Wiley & Sons, Inc., NY (1991).

Preferred amino protecting groups include, but are not limited to, benzyloxycarbonyl (CBz), t-butyl-oxycarbonyl (Boc), t-butyldimethylsilyl (TBDMS), 9-fluorenylmethyl-oxycarbonyl (Fmoc), or suitable photolabile protecting groups, such as 6-nitroveratryloxy carbonyl (Nvoc), nitropiperonyl, pyrenylmethoxycarbonyl, nitrobenzyl, dimethyl dimethoxybenzyl, 5-bromo-7-nitroindolinyl and the like. Preferred hydroxyl protecting groups include Fmoc, TBDMS, photolabile protecting groups, such as nitroveratryl oxymethyl ether (Nvom)), Mom (methoxy methyl ether) and Mem (methoxy ethoxy methyl ether). Particularly preferred protecting groups include NPEOC (4-nitrophenethyloxycarbonyl) and NPEOM (4-nitrophenethyloxy-methyloxycarbonyl).

It will be appreciated that the compounds of the invention, e.g., the compounds of formula (I), may exist in the form of optical isomers, racemates or diastereoisomers. For example, a compound of formula (I) wherein $R_2$ and $R_3$ are different residues, is asymmetric and may have the R— or S— configuration. It is to be understood that the present invention embraces all enantiomers and their mixtures. Similar considerations apply in relation to starting materials exhibiting asymmetric carbon atoms as mentioned.

The compounds of the invention, e.g., the compounds of formula (I), may exist in free form or in salt form, e.g., in form of a pharmaceutically acceptable salt. A "pharmaceutically acceptable salt" of a compound means a physiologically and pharmaceutically acceptable salt that possesses the desired pharmacological activity of the parent compound and does not impart undesired toxicological effects. Such salts include:
1. Acid addition salts, formed with inorganic acids, such as hydrochloric acid, hydrobromic acid, sulfuric acid, nitric acid, phosphoric acid and the like; or formed with organic acids, such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid and the like; or
2. Salts formed when an acidic proton present in the parent compound either is replaced by a metal ion, e.g., an alkali metal ion, an alkaline earth ion or an aluminum ion; or coordinates with an organic base, such as ethanolamine, diethanolamine, triethanolamine, tromethamine, N-methylglucamine and the like.

A compound of the invention, e.g., a compound of formula (I), may act as a prodrug. Prodrug means any compound which releases an active parent drug according to formula (I) in vivo when such prodrug is administered to a mammalian subject. Prodrugs of a compound of formula (I) are prepared by modifying functional groups present in the compound of formula (I) in such a way that the modifications may be cleaved in vivo to release the parent compound. Prodrugs include compounds of formula (I) wherein a hydroxy, amino or sulfhydryl group in compound (I) is bonded to any group that may be cleaved in vivo to regenerate the free hydroxyl, amino or sulfhydryl group, respectively. Examples of prodrugs include, but are not limited to, esters, e.g., acetate, formate and benzoate derivatives; carbamates, e.g., N,N-dimethylamino-carbonyl; of hydroxy functional groups in compounds of formula (I) and the like.

In the compounds of the invention, e.g., the compounds of formula (I), the following significances are preferred individually or in any subcombination:
1. Y is COOH, SH, —CO—NH(OH) or —N(OH)CHO, preferably —CO—NH(OH).
2. X is —CH$_2$—.
3. $R_2$ is hydroxy, fluorine or hydrogen.
4. $R_3$ is hydrogen.
5. W is CR$_4$R$_5$ wherein $R_4$ is hydrogen and $R_5$ is hydrogen or C$_{1-10}$alkyl, preferably n-butyl;
6. n is 1.
7. $R_1$ is phenyl or heteroaryl.
8. Heteroaryl as $R_1$ is oxazolyl, thiazolyl, pyridinyl and benzimidazolyl. When heteroaryl is oxazolyl, the oxazolyl may be substituted with a lower alkyl, especially methyl. When the heteroaryl is thiazolyl, the thiazolyl may be substituted by one or two substituents selected from the group consisting of lower alkyl and phenyl. Preferably $R_1$ is oxazolyl or methyloxazolyl.
9. $R_1$ is preferably linked to the α-position of the azacycloalkane represented in formula (I).

Compounds of the invention, e.g., the compounds of formula (I), may be prepared in accordance with methods well-known in the art of organic chemistry. Compounds of formula I may be prepared by reacting a compound of formula II

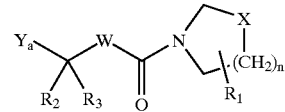

(II)

wherein X, $R_1$, $R_2$, $R_3$, W and n are as defined above and $Y_a$ is COOH or a functional derivative thereof, with a hydroxylaminating agent, e.g., NH$_2$OH and, where required, converting the resulting compounds obtained in free form into salt forms or vice versa.

Functional derivatives of COOH as $Y_a$ are, e.g., halogenides, e.g., acid chloride, esters or acid anhydride.

Above reaction may be carried out according to methods known in the art or as disclosed in Schemes A to K and in the examples below.

Insofar as the production of starting materials is not particularly described, the compounds are known or may be prepared analogously to methods known in the art or as disclosed in the examples hereinafter.

The following abbreviations are used:
AcOH=acetic acid
BuLi=n-butyl lithium
DAST=diethylaminosulfur trifluoride
DCC=dicyclohexylcarbodiimide
DCE=dichloroethane
DCM=dichloromethane
DIC=diisopropylcarbodiimide
DIAD=diisopropylazodicarboxylate
DIEA=diisopropylethylamine DME=1,2-dimethoxyethane
DMF=dimethylformamide
DMSO=dimethylsulfoxide
EDC=N-(3-dimethylaminopropyl)-N'-ethylcarbodiimide
EtOAc=ethyl acetate
HATU=O-(7-aza-benzotriazol-1-yl)-N, N, N',N'-tetramethyluronium hexafluorophosphate
LDA=lithium diisopropylamine
MeOH=methanol
NaHMDS=sodium hexamethyldisilazide
PyBOP=benzotriazole-1-yl-oxy-tris-pyrrolidinophosphonium hexafluorophosphate
rt=room temperature
TEA=triethylamine
TFA=trifluoroacetic acid
THF=tetrahydrofuran
p-TSA=p-toluenesulfonic acid
TMSCl=trimethylsilyl chloride General Procedure A Synthesis of N-hydroxy-3-aminocarbonylpropionamide

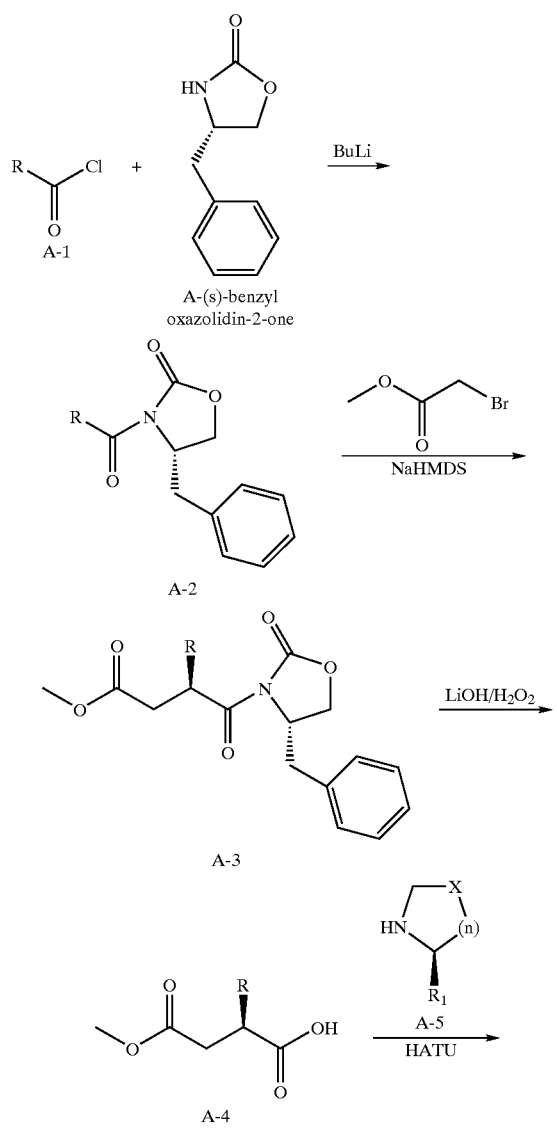

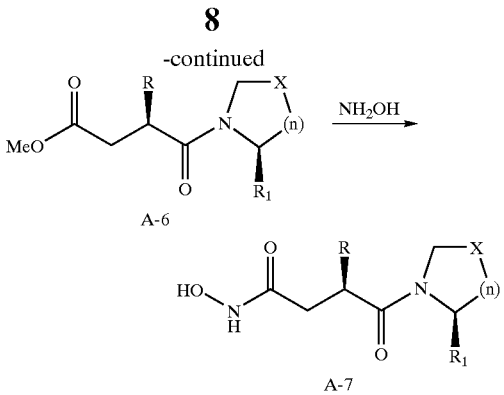

Step 1: To a solution of 4-(S)-benzyloxazolidin-2-one (56 mmol) (Aldrich, Milwaukee, Wis.) in THF at −78° C. is added 2.5 M n-BuLi in hexane (22.4 mL, 56 mmol) and the reaction is stirred at −78° C. for 2 hours. To this is added via cannula a −78° C. solution of acid chloride A-1 (R=hexanoyl, 65 mmol) in THF and the mixture is stirred at −78° C. for 2 hours, then allowed to warm to rt and stirred overnight. The reaction is then quenched with aqueous saturated $NH_4Cl$, extracted with EtOAc, dried and purified by silica gel chromatography (hexanes/EtOAc) to afford N-hexanoyl-4-(S)-benzyloxazolidin-2-one (A-2).

Step 2: To a solution of N-hexanoyl-4-(S)-benzyloxazolidin-2-one A-2 (7.3 mmol) in THF at −78° C. is added 1.0 M NaHMDS (8.8 mmol) and the reaction stirred at −78° C. for 1 hour. A solution of methyl bromoacetate (8.8 mmol) in THF is then added dropwise, and the resulting mixture is stirred at −78° C. for 1 hour and then at rt overnight. The reaction is quenched with $NH_4Cl$, concentrated, then suspended in EtOAc and washed with 0.5 N HCl and brine, dried and purified by silica gel chromatography (EtOAc/hexanes) to afford the methyl 3-(R)-(n-butyl)-3-[4-(S)-benzyloxazolidin-2-one-3-ylcarbonyl)propionate (A-3).

Step 3: To methyl 3-(R)-(n-butyl)-3-[4-(S)-benzyloxazolidin-2-one-3-ylcarbonyl)-propionate A-3 (1.44 mmol) in THF/water at 0° C. is added 30% $H_2O_2$ (5.76 mmol) and solid lithium hydroxide (1.44 mmol) and the reaction is stirred at 0° C. for 3 hours. The reaction is then quenched with 2.0 M $Na_2SO_3$, concentrated, suspended in EtOAc and subjected to standard aqueous workup. The crude product is purified by silica gel chromatography (MeOH/DCM) to afford methyl 3-(R)-(n-butyl)-propionate (A-4).

Step 4: To a solution of mono-protected succinate, e.g., mono-4-methyl 2-(R)-butylsuccinic acid A-4 (1 mmol) in DMF is added amine A-5 (1 mmol), DIEA (0.4 mL, 2.3 mmol), and an activating reagent (e.g,. EDC, PyBOP, DIC, DCC, etc.; 1 mmol). The mixture is stirred overnight, then diluted with EtOAc and washed with aqueous HCl (1 N), water, saturated $NaHCO_3$, brine and then dried ($Na_2SO_4$). The filtrate is concentrated and then purified on silica gel (Merck 60; EtOAc/hexane) to afford 3-aminocarbonylpropionate A-6.

Step 5: 3-aminocarbonylpropionate A-6 (0.1 mmol) is treated with dioxane (1 mL) and hydroxylamine (50% in water, 2 mL) for 1–3 days, and then purified by preparative reverse-phase (C18) HPLC to afford the desired N-hydroxy-3-aminocarbonylpropionamide (A-7).

General Procedure B

Synthesis of 2(S)-hydroxy-3(R)-[2(S)-oxazol-2-yl-pyrrolidine-1-carbonyl)-heptanoic acid hydroxamide Step 1: To a solution of diisopropylamine (14 mL, 100 mmol) in THF at 0° C. is added BuLi (2.5 M in hexane, 40 mL, 100 mmol) over 10 minutes. The mixture is stirred at rt for 30 minutes, and then added via cannula to a −78° C. solution of dimethyl malate B-1 (7.71 g, 47.6 mmol) in THF (130 mL). The mixture is warmed to −20° C. over 2 hours, and then cooled to −78° C. Crotyl bromide (8.1 g, 60 mmol) is added, then the mixture is allowed to warm to rt and then stirred overnight. The solution is then cooled to −10° C. and quenched with NH$_4$Cl (10%, 100 mL). The THF is removed and the residue extracted with EtOAc (2×200 mL). The combined organic layers are washed with HCl (1 N, 3×50 mL), saturated aqueous NaHCO$_3$ (3×50 mL), and brine, then dried over Na$_2$SO$_4$. The solution is filtered and concentrated to give a residue, which is purified on silica gel (EtOAc/hexane 1:4) to afford (2S,3R)-3-(2-butenyl)-2-hydroxysuccinic dimethyl ester B-2.

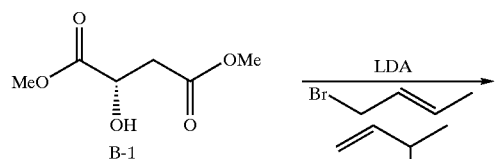

B-1

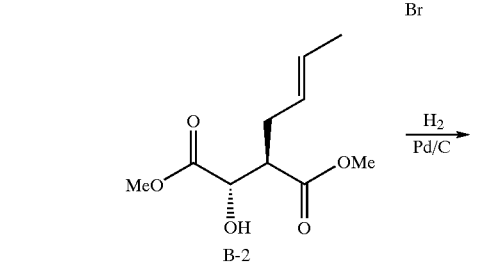

B-2

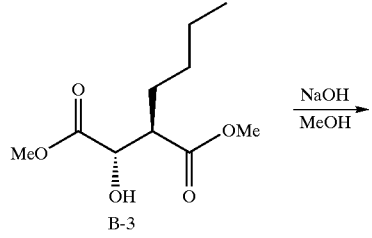

B-3

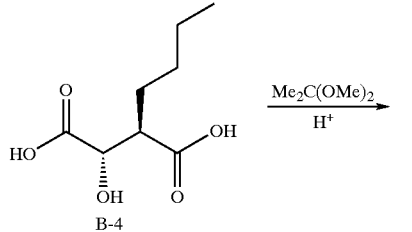

B-4

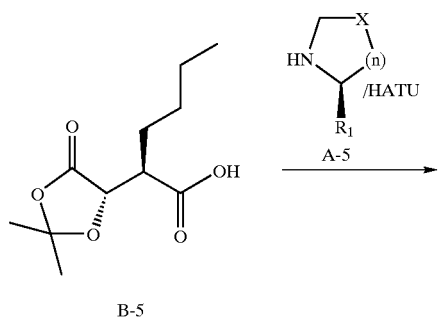

B-5

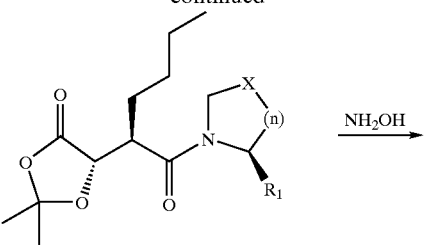

B-6

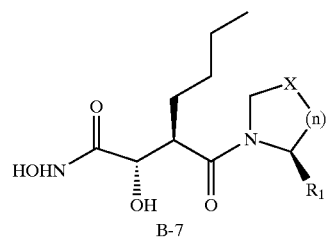

B-7

Step 2: To (2S,3R)-3-(2-butenyl)-2-hydroxysuccinic dimethyl ester B-2 (2.5 g) in EtOAc (50 mL) is added 10% Pd/C (0.25 g) and the reaction stirred under a hydrogen atmosphere for 20 hours. The suspension is filtered through Celite, washed with EtOAc (3×) and then concentrated in vacuo to afford (2S,3R)-3-(n-butyl)-2-hydroxysuccinic dimethyl ester B-3.

Step 3: To (2S,3R)-3-(n-butyl)-2-hydroxysuccinic dimethyl ester B-3 in MeOH (28 mL) is added a solution of NaOH (2.2 g, 55 mmol) in water (28 mL). After 24 hours, the MeOH is removed, the crude reaction is acidified with HCl (6 N, 12 mL) to pH=1, and then extracted with EtOAc (3×50 mL). The combined organic layers are dried (Na$_2$SO$_4$) and concentrated to give (2S,3R)-3-(n-butyl)-2-hydroxysuccinic acid B-4.

Step 4: To a solution of (2S,3R)-3-(n-butyl)-2-hydroxysuccinic acid B-4 (300 mg, 1.58 mmol) in 2,2-dimethoxypropane (10 mL) is added p-TSA (20 mg) and the reaction is stirred at rt for 16 hours. The solution is diluted with DCM and washed with brine, dried (Na$_2$SO$_4$) and then purified by silica gel chromatography to afford 1.2 mmol 2-(2,2-dimethyl-4-oxo-1,3-dioxolan-5-yl)hexanoic acid B-5.

Step 5: To a solution of 2-(2,2-dimethyl-4-oxo-1,3-dioxolan-5-yl)hexanoic acid B-5 (1.2 mmol) in DMF (10 mL) is added bicyclic pyrrolidine A-5 (1.2 mmol), HATU (1.2 mmol), and DIEA (2.5 mmol). The mixture is stirred overnight, then concentrated and purified on silica gel (EtOAc/hexane 1:4) to afford 275 mg of the desired amide B-6.

Step 6: To a cold solution of B-6 in dioxane (5 mL) 50% aqueous hydroxylamine is added (400 μL), and the solution stirred at 4° C. for 8 hours. The crude reaction mixture is then purified by preparative reverse-phase (C18) HPLC to afford 2(S)-hydroxy-3(R)-[2(S)-oxazol-2-yl-pyrrolidine-1-carbonyl)-heptanoic acid hydroxamide B-7.

General Procedure C

Synthesis of 2-fluoro-3-(R)-(2-S-oxazol-2-yl-pyrrolidine-1-carbonyl)-heptanoic acid hydroxamide

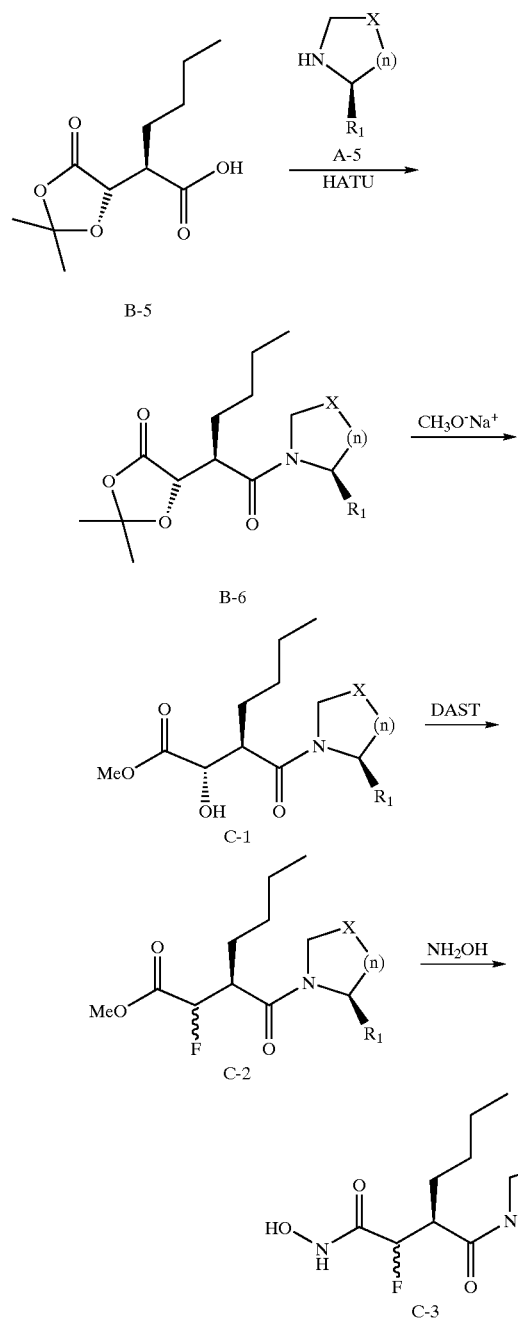

Step 1: To 2,2-dimethyl-5-[2(S)-oxazol-2-yl-pyrrolidin-1-carbonyl)-pentyl]-[1,3]dioxolan-4one B-6 (5 mmol, 50%) (5 mmol) in MeOH (20 mL) is added sodium methoxide (catalytic; pH adjusted to 10) and the solution stirred for 1 hour. Amberlite IR-120 resin (H+ form) is added, then the solution is filtered and concentrated to afford 2(S)-hydroxy-3-(2(S)-oxazol-2-yl-pyrrolidin-1-carbonyl)-heptanoic acid methyl ester C-1.

Step 2: To 2(S)-hydroxy-3-(2(S)-oxazol-2-yl-pyrrolidin-1-carbonyl)-heptanoic acid methyl ester C-1 (5 mmol) in DCM (5 mL) is added DAST (15 mmol) at −20° C. The solution is stirred for 16 hours at rt. The reaction mixture is washed with aqueous NaHCO₃ and brine, dried (Na₂SO₄) and concentrated then purified on silica gel (EtOAc/hexanes) to afford 2-(R/S)-fluoro-3-(2(S)-oxazol-2-yl-pyrrolidin-1-carbonyl)-heptanoic acid methyl ester C-2.

1H NMR analysis of this product suggested approximately 1:2 ratio of S/R diastereomers. The two isomers are separated by silica gel column chromatography.

Step 3: To intermediate C-2 (0.15 mmol, each isomer is treated separately) in dioxane (1 mL), aqueous 50% hydroxylamine is added (0.5 mL) and the reaction stirred for 16 hours at 5° C. The crude reaction mixture is then purified by preparative reverse-phase (C18) HPLC to afford 2-fluoro-3-(R)-(2-S-oxazol-2-yl-pyrrolidine-1-carbonyl)-heptanoic acid hydroxamide C-3.

General Procedure D

N-hydroxy-N-{2-R-[2-S-(oxazol-2-yl)-pyrrolidine-1-carbonyl]-hexyl}-formamide

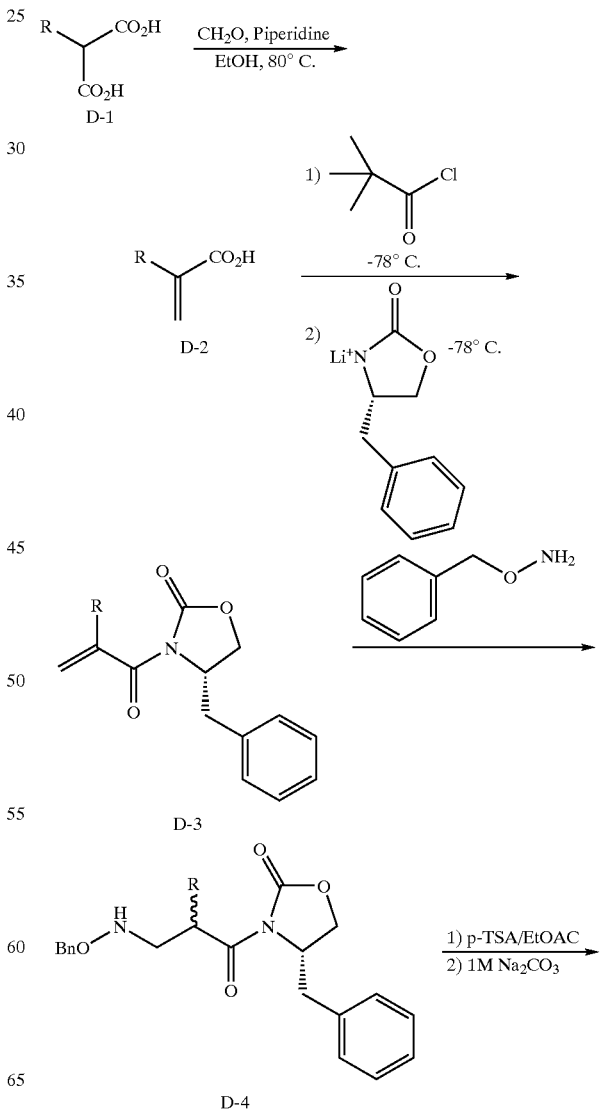

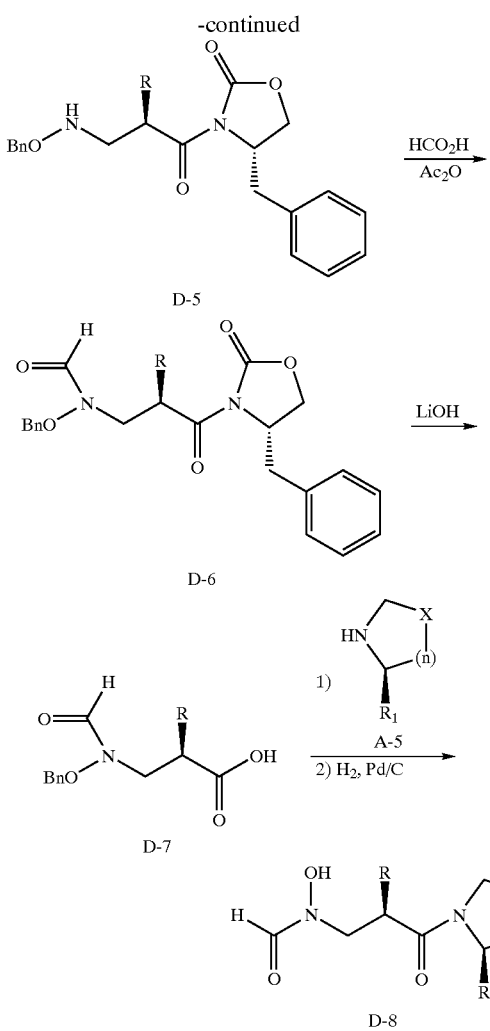

Step 1: 2-n-butyl acrylic acid (D-2) (R=n-butyl) is prepared as indicated above.

Step 2: 4-benzyl-3-(2-butyl-acryloyl)-oxazolidin-2-one (D-3)

2-n-butyl acrylic acid (9.90 g, 77.2 mmol, 1 equiv.) is dissolved in dry THF (260 ml) and cooled to −78° C. under a blanket of nitrogen. Hunig's base (17.5 mL, 100.4 mmol, 1.3 equiv.) and pivaloyl chloride (9.5 mL, 77.2 mmol, 1 equiv.) are added at such a rate that the temperature remained below −60° C. The mixture is stirred at −78° C. for 30 minutes, warmed to rt for 2 hours, and finally cooled back to −78° C.

In a separate flask, (S)-(−)4-benzyl-2-oxazolidinone (13.49 g, 77.24 mmol) is dissolved in dry THF (150 mL) and cooled to −78° C. under nitrogen. BuLi (2.5 M solution in hexanes, 30.9 mL, 77.2 mmol, 1 equiv.) is added slowly at −78° C., and the mixture is stirred for 30 minutes at rt. The resulting anion is slowly transferred via a cannula into the original reaction vessel. The mixture is allowed to warm to rt and is stirred overnight at rt. The reaction is quenched with 1 M $KHCO_3$, and the solvents are removed under reduced pressure. The residue is partitioned between EtOAc and water. The organic layer is washed with brine, dried over anhydrous $Na_2SO_4$, filtered and concentrated to give a yellow oil which is purified by flash chromatography (hexane:EtOAc=4:1) to yield the title compound D-3 as a white solid.

1H NMR ($CDCl_3$): δ 7.39–7.20 (m, 5H), 5.42–5.40 (d, J=7.14 Hz, 2H), 4.76–4.68 (m, 1H), 4.29–4.156 (m, 2H), 3.40–3.35 (dd, J=3.57, 13.46 Hz, 1H), 2.86–2.79 (dd, J=9.34, 13.46 Hz, 1H), 2.42–2.37 (t, J=7.69 Hz, 2H), 1.55–1.30 (m, 4H), 0.951–0.904 (t, J=7.14 Hz, 3H). ES-MS: calcd. For $C_{17}H_{21}NO_3$ (287.35); found: 288.5 [M+H].

Step 3: 4-benzyl-3-[2-(benzyloxyamino-methyl)-hexanoyl]-oxazolidin-2-one (p-toluenesulfonic acid salt)

Compound D-3 (8.25 g, 28.7 mmol) is mixed with O-benzylhydroxylamine (7.07 g, 57.4 mmol, 2 equiv.) and stirred for 40 hours at rt under nitrogen. The mixture is dissolved in EtOAc and p-TSA (21.84 g, 114.8 mmol, 4 equiv.) is added to precipitate excess O-benzylhydroxylamine as a white solid. The white solid is filtered off, and the filtrate is concentrated to give a crude yellow oil. Charging the crude yellow oil with excess diethyl ether and cooling to 0° C. for 30 minutes gave a solid which is collected by filtration and dried in vacuo to afford the title compound as a white crystalline solid (single diastereomer).

1H NMR ($CDCl_3$): δ 8.07–8.04 (d, J=8.24 Hz, 2H), 7.59–7.39 (m, 10H), 7.18–7.15 (d, J=7.69 Hz, 2H), 5.49–5.40 (q, J=8.61 Hz, 2H), 4.65–4.56 (m, 1H), 4.25–4.08 (m, 3H), 3.83–3.79 (d, J=13.46 Hz, 1H), 3.15–3.11 (d, J=13.46 Hz, 1H), 2.56 (s, 3H), 1.83–1.67 (m, 4H), 1.40 (bs, 4H), 1.00–0.951 (t, J=6.87, 3H). ES-MS: calcd. For $C_{24}H_{30}N_2O_4 \cdot C_7H_8O_3S$ (582.71); found: 411.7 [M+H] free base.

Step 4: 4-benzyl-3-[2-(benzyloxyamino-methyl)-hexanoyl]-oxazolidin-2-one (D-5)

To a solution of p-TSA salt (22.9 g, 39.3 mmol) dissolved in EtOAc (400 mL), is added 1 M $Na_2CO_3$ (200 mL, 5 equiv.) and stirred at rt for 30 minutes. The layers are separated, and the aqueous layer extracted with EtOAc. The combined organic layers are dried over anhydrous $Na_2SO_4$, filtered and concentrated to give the title compound as a pale opaque oil.

1H NMR ($CDCl_3$): δ 7.57–7.38 (m, 10H), 4.98–4.90 (m, 2H), 4.87–4.79 (m, 1H), 4.38–4.28 (m, 3H), 3.64–3.57 (dd, J=9.21, 12.64 Hz, 1H), 3.46–3.36 (td, J=3.76, 13.05 Hz, 2H), 2.68–2.60 (dd, J=10.03, 13.46 Hz, 1H), 1.90–1.88 (m, 1H), 1.78–1.71 (m, 1H), 1.51–1.44 (m, 4H), 1.10–1.06 (t, J=6.73 Hz, 3H). ES-MS: calcd. For $C_{24}H_{30}N_2O_4$ (410.51); found: 411.7 [M+H].

Step 5: N-[2-(4-benzyl-2-oxo-oxazolidine-3-carbonyl)-hexyl]-N-benzyloxy-formamide (D-6)

A solution of compound D-5 (5.38 g, 13.1 mmol, 1 equiv.) in formic acid (7.4 mL, 196.6 mmol, 15 equiv.) is cooled to 0° C. under nitrogen. In a separate flask, formic acid (7.4 ml, 196.6 mmol, 15 equiv.) is cooled to 0° C. under nitrogen, and acetic anhydride (2.47 mL, 26.2 mmol, 2 equiv.) is added dropwise. The solution is stirred at 0° C. for 15 minutes. The resulting mixed anhydride is slowly transferred via syringe into the original reaction vessel. The mixture is stirred at 0° C. for 1 hour, then at rt for 3 hours. The mixture is concentrated, taken up in DCM, and washed successively with saturated $NaHCO_3$ and brine. The organic layer is dried over anhydrous $Na_2SO_4$, filtered and concentrated to give an opaque oil which is purified by flash chromatography (hexane:EtOAc=2:1 then DCM:acetone=9:1) to yield the title compound as a colorless oil.

1H NMR ($CDCl_3$, rotamers): δ 8.38 (s, 0.7H), 8.21 (s, 0.3H), 7.54–7.35 (m, 10H), 5.0–5.00 (m, 2H), 4.88–4.81 (m, 1H), 4.39–4.29 (m, 4H), 4.07–4.03 (m, 1H), 3.43–3.39 (m, 1H), 2.66–2.58 (m, 1H), 1.89 (bs, 1H), 1.73 (bs, 1H), 1.49–1.44 (m, 3H), 1.10–1.06 (t, J=6.73 Hz, 3H). ES-MS: calcd. For $C_{25}H_{30}N_2O_5$ (438.52); found: 439.7 [M+H].

Step 6: 2-[(benzyloxy-formyl-amino)-methyl]-hexanoic acid (D-7)

Compound D-6 (0.163 g, 0.372 mmol, 1 equiv.) is dissolved in THF (4.5 mL) and water (1.5 mL) and cooled to 0° C. Hydrogen peroxide (30% in water, 228 μL, 2.23 mmol, 6 equiv.) is added dropwise followed by the slow addition of a solution of lithium hydroxide (0.019 g, 0.446 mmol, 1.2 equiv.) in water (350 μL). The resulting mixture is stirred at 0° C. for 1.5 hours. The basic reaction mixture is quenched with Amberlite IR-120 resin (H+) to pH 4–5 at 0° C. The resin is filtered off and rinsed with EtOAc. The mixture is concentrated to remove THF, and then taken up in EtOAc. The aqueous layer is separated, and the organic layer dried over anhydrous Na$_2$SO$_4$, filtered and concentrated to give an opaque oil which is purified by flash chromatography (DCM:acetone=4:1 then acetone:MeOH=99:1) to yield the title compound D-7 as a colorless oil.

1H NMR (DMSO-d$_6$, rotamers): δ 11.2 (s,1H), 8.20 (s, 0.2H), 7.95 (s, 0.8H), 7.33–7.41 (m, 5H), 4.87 (s, 2H), 3.71 (bs, 2H), 2.50 (bs, 1H), 1.35–1.45 (m, 2H), 1.14–1.28 (m, 4H), 0.857–0.813 (t, J=13.1 Hz, 3H). ES-MS: calcd. For C$_{15}$H$_{21}$NO$_4$ (279.33); found: 278.5 [M−H], 302.5 [M+Na].

Step 7: 1-{2-[(benzyloxy-formyl-amino)-methyl]-hexanoyl}-pyrrolidine-2-carboxylic acid amide To a solution of compound D-7 (0.190 g, 0.680 mmol, 1 equiv.) in dry dioxane (4 mL) at rt under nitrogen is added successively Hunig's base (391 μL, 2.24 mmol, 3.3 equiv.), compound A-5 (0.748 mmol, 1.1 equiv.) and HATU (0.284 g, 0.748 mmol, 1.1 equiv.). The resulting mixture is stirred at rt for 22 hours. The mixture is partitioned between EtOAc and 10% citric acid. The organic layer is washed with brine and saturated NaHCO$_3$, dried over anhydride Na$_2$SO$_4$, filtered and concentrated. The residue is purified by flash chromatography (DCM:acetone=3:1) to give the title compound as a colorless oil.

Step 8: {2-[(formyl-hydroxy-amino)-methyl]-hexanoyl}-pyrrolidine-2-carboxylic acid amide (D-8)

Pd—C (0.059 g, 0.1 equiv.) is added to a solution of above compound (0.550 mmol, 1 equiv.) in a 1:1 EtOAc/ethanol solution (12 mL) under nitrogen. The mixture is stirred under hydrogen atmosphere for 36 hours. The catalyst is removed by filtration through Celite. The filtrate is concentrated, and the residue is purified by preparative TLC (DCM:acetone=2:1) to give the title compound as an amorphous solid.

General Procedure E

Synthesis of 2-pyrrolidine-2-yl-oxazole (hydrobromic acid salt)

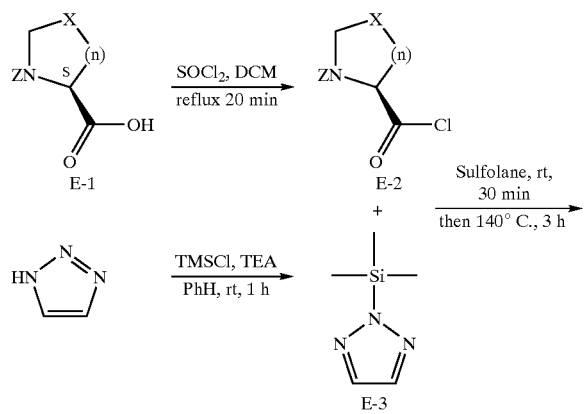

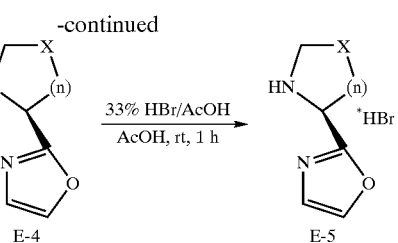

2-(S)-pyrrolidin-2-yl-oxazole E-5 (X=CH$_2$, n=1) is prepared as described below.

Step 1: 2-chlorocarbonyl-pyrrolidine-1-carboxylic acid benzyl ester (E-2)

A mixture of Z-L-Pro-OH E-1 (10.0 g, 40.1 mmol, 1 equiv.) and thionyl chloride (30 mL, 401.2 mmol, 10 equiv.) in DCM (200 mL) is heated to reflux under nitrogen for 20 minutes and concentrated in vacuo. The residual oil is coevaporated with toluene 3×, and concentrated to give Z-L-Pro-Cl as an opaque oil.

Step 2: 2-(trimethyl-silanyl)-2H-[1,2,3]triazole (E-3)

To a solution of 1H-1,2,3-triazole (4.98 g, 72.10 mmol, 1 equiv.) in dry benzene (145 mL) at rt under nitrogen, is added TEA (11.05 mL, 79.31 mmol, 1.1 equiv.) followed by the dropwise addition of TMSCl (9.15 mL, 72.10 mmol, 1 equiv.). A white precipitate develops. Reaction mixture is stirred at rt under nitrogen for 1 hour. The resultant precipitate is removed by filtration and washed thoroughly with dry benzene. The filtrate is gently concentrated to avoid evaporating the highly volatile product to give a quantitative yield of TMS-triazole with a trace of benzene.

Step 3: 2-oxazol-2-yl-pyrrolidine-1-carboxylic acid benzyl ester (E-4)

To a solution of TMS-triazole (14.17 g, 100.3 mmol, 1 equiv.) in sulfolane (290 mL) at rt under nitrogen, is added dropwise Z-L-Pro-Cl (26.85 g, 100.3 mmol, 1 equiv.) in sulfolane (70 mL). The resulting mixture is stirred at rt for 30 minutes, then the temperature is elevated to 140° C. for 3 hours. After the reaction mixture is cooled to rt, poured into excess brine and extracted with diethyl ether. The diethyl ether extracts are washed with brine, dried over anhydrous Na$_2$SO$_4$, filtered and evaporated. The residue is purified by flash chromatography (DCM:acetone=9:1) to give the title compound as a light yellow oil.

1H NMR (CDCl$_3$): δ 7.79–7.70 (s, 1H), 7.67–7.47 (m, 5H), 7.37–7.23 (m, 1H), 5.42–5.19 (m, 2H), 3.92–3.69 (m, 2H), 2.49–2.14 (m, 5H). ES-MS: calcd. for C$_{15}$H$_{16}$N$_2$O$_3$ (272.30); found 273.5 [M+H].

Step 4: 2-pyrrolidin-2-yl-oxazole (hydrobromic acid salt) (E-5)

A solution of compound E-4 (6.33 g, 23.25 mmol, 1 equiv.) in AcOH (116 ml) at rt is treated with HBr (5.7 M, 33% in AcOH, 204 ml, 1162 mmol, 50 equiv.), and the mixture is stirred at rt for 1 hour. Charging the reaction mixture with excess diethyl ether and cooling to 0° C. for 30 minutes gives a solid which is collected by filtration and dried in vacuo to afford the title compound as a brownish powder.

1H NMR (DMSO-d$_6$): δ 9.98 (bs, 1H), 8.47 (s, 1H), 7.53 (s,1H), 5.14–5.05 (m, 1H), 3.54–3.46 (m, 2H), 2.62–2.53 (m, 1H), 2.43–2.33 (m, 1H), 2.28–2.15 (m, 2H). ES-MS: calcd. for C$_7$H$_{10}$N$_2$O*HBr (219.08); found: 139.4 [M+H] free base.

General Procedure F

Synthesis of 5-alkyl-2(S)-pyrrolidine-2-yl-oxazole

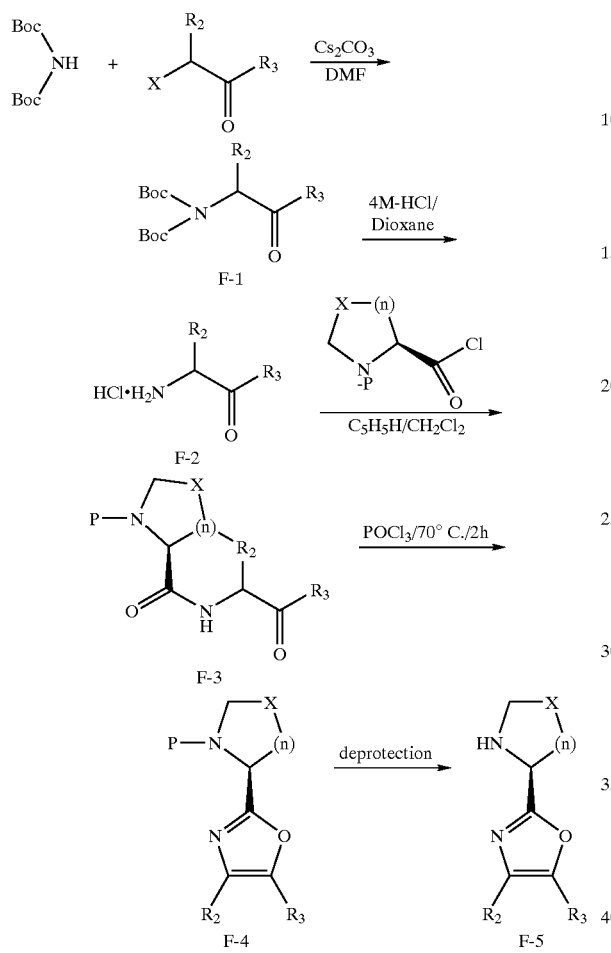

P = Trifluoracetyl Benzyloxycarbonyl 5-methyl-2-(S)-pyrrolidin-2-yl-oxazole (F-5)

A solution of (S)-N-(trifluoroacetyl)prolyl chloride (Aldrich) 1 equiv. in DCM is treated with 1-amino-propan-2-one (1.5 equiv.) in pyridine at rt for 5 hours. After usual work up, it provides 1-trifluoroacetyl-pyrrolidine-2-carboxylic acid (2-oxo-propyl)-amide.

1H NMR (CDCl$_3$): δ 4.55–4.50 (m, 1H), 4.15 (s, 2H), 3.78–3.69 (m, 2H), 2.18 (s, 3H), 2.15–1.85 (m, 4H).

Treatment of this intermediate with POCl$_3$ at 70° C. for 2 hours provides 2,2,2-trifluoro-1-{2(S)-(5-methyl-oxazol-2-yl)-pyrrolidin-1-yl}-ethanone.

Treatment of this material with 2 M methanolic ammonia for 5 hours affords title compound.

MS: m/z=153.4 (M+1).

General Procedure G

Synthesis of 2-(alkylated-thiazole)-2-pyrrolidine

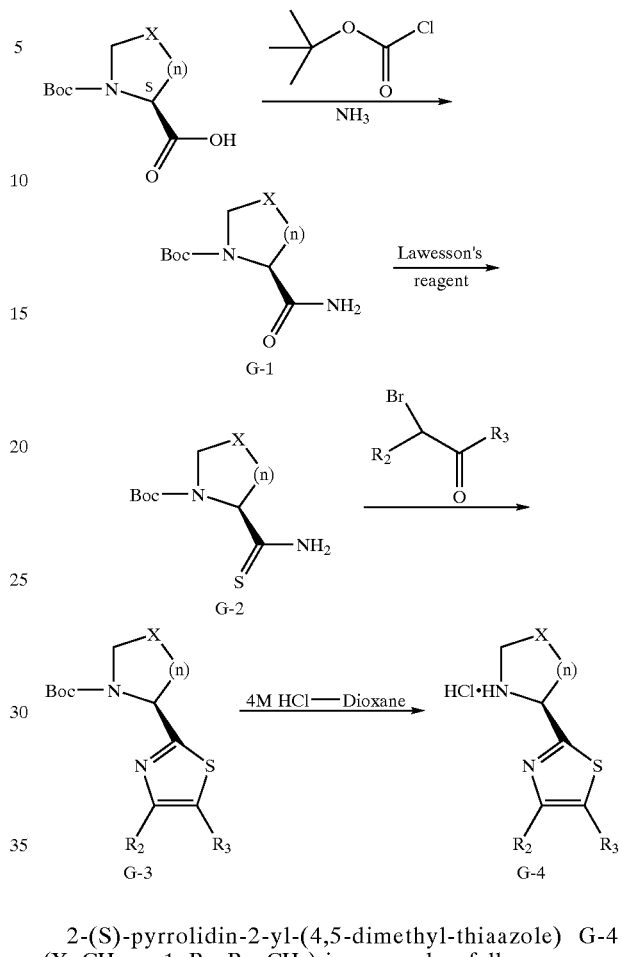

2-(S)-pyrrolidin-2-yl-(4,5-dimethyl-thiaazole) G-4 (X=CH$_2$, n=1, R$_2$=R$_3$=CH$_3$) is prepared as follows:

To a solution of thioamide G-2 (0.11 g, 1 equiv.) in DME (5 mL) is added 3-bromo-2-butanone (0.16 mL, 3 equiv.) and KHCO$_3$ (0.40 g, 8 equiv.) and stirred for 2 hours. The reaction mixture is cooled to 0° C., then pyridine (0.4 mL, 8.5 equiv.) and trifluoroacetic anhydride (0.32 mL, 4 equiv.) is added and the mixture is stirred at rt 16 hours. It is diluted with EtOAc and washed with water, brine, dried (Na$_2$SO$_4$) and concentrated under reduced pressure. The residue is purified by silica gel chromatography using hexane-EtOAc (1:1) as solvent gradient to give the desired intermediate.

1H NMR (CDCl$_3$): δ 5.18–4.86 (m, 1H), 3.68–3.43 (m, 2H), 2.35 & 2.30 (each s, 2×3H), 2.15–1.81 (m, 2H), 2.54–1.45 (m, 2H), 1.35, (s, 9H). ES-MS: calcd. for C$_{14}$H$_{22}$N$_2$O$_2$ S (282.14); found: 283.3 [M+1].

Treatment of above compound with 4 M HCl in dioxane provides the title compound.

2-(S)-pyrrolidin-2-yl-(5-phenyl-thiaazole) G-4 (X=CH$_2$, n=1, R$_2$=C$_6$H$_5$, R$_3$=H) is prepared reacting a solution of thioamide G-2 (0.13 g, 1 equiv.) in DME (5 mL) with 2-bromo-acetophenone (0.34 g, 3 equiv.) and KHCO$_3$ (0.45 g, 8 equiv.) and further working up as disclosed above.

1H NMR (CDCl$_3$): δ 8.25–8.15 (m, 3H), 7.71–7.45 (m, 3H), 5.39–5.22 (dd, J=2.8 Hz, 1H), 3.79–3.65 (m, 2H), 2.59–2.41 (m, 1H), 2.38–2.22 (m, 1H), 2.19–2.12 (m, 2H), 1.551 (bs, 9H). ES-MS: calcd. for C$_{18}$H$_{22}$N$_2$O$_2$ S (330.45); found: 331.5 [M+1].

Treatment of above compound with 4 M HCl in dioxane provides the title compound.

General Procedure H
Synthesis of 2-pyrrolidin-2-yl-benzimidazole

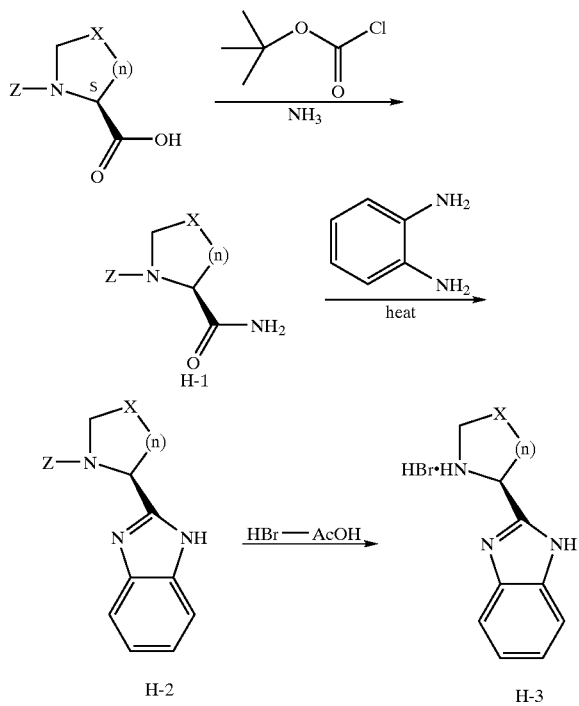

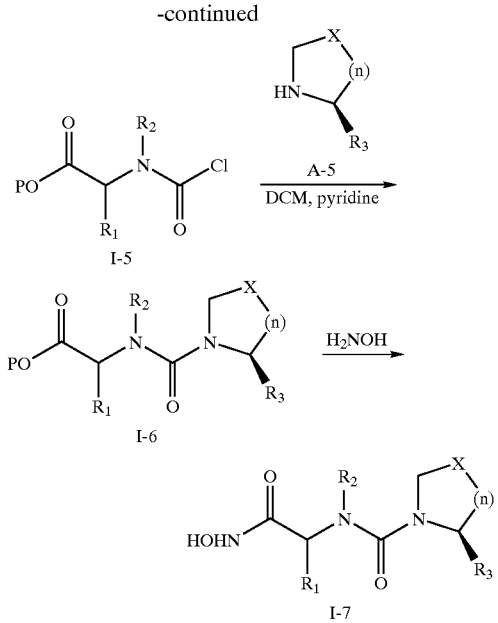

P = Me

N-Cbz-L-Proline amide [X=CH$_2$, n=1] (4 g, 16.1 mmol) and o-phenylenediamine (1.7 g, 15.5 mmol) are heated to 165° C. in a nitrogen atmosphere for 2.5 hours then the temperature is increased to 220° C. for an additional 40 minutes. The reaction mixture is cooled to rt and dissolved in DCM and washed with saturated NaHCO$_3$, water and brine then dried over MgSO$_4$ and evaporated to dryness. The residue is recrystallized from 2:1/PrOH/water then diethyl ether/hexanes to provide the Cbz-protected benzimidazole 630 mg. The protected material is then taken up in AcOH (3 mL) and 33% HBr in AcOH (6 mL) is added. After 40 minutes, diethyl ether is added and the solution cooled to 0° C. the precipitate is collected on a glass filter. Recrystalization from MeOH/diethyl ether provides the title compound as HBr salt.

1H NMR (CDCl$_3$): δ 7.63 (dd, J=3.3, 6.3, 2H), 7.43 (dd, J=3.0, 6.3, 2H), 5.13 (dd, J=8.0, 8.0, 1H), 4.57–3.37 (m, 2H), 2.64–2.58 (m, 1H), 2.43–2.04 (m, 3H). ES-MS: calcd. for C$_{11}$H$_{13}$N$_3$ (187.1); found: 188.1 [M+H].

General Procedure I

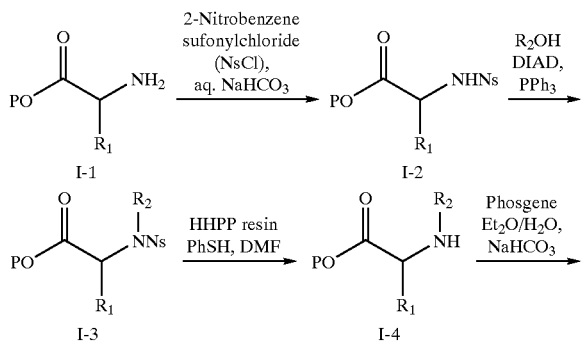

Step 1
To an aminoacid methyl ester hydrochloride I-1 (P=methyl, R$_1$=H, 88 mmol) in saturated aqueous NaHCO$_3$ (25 mL) is added with vigorous stirring a solution of 2-nitrobenzene-sulfonyl chloride (77 mmol) in THF (50 mL). Additional NaHCO$_3$ is added over 2 hours to maintain a basic pH. The reaction mixture is then extracted with DCM (500 mL) and the organic layer washed with water, dried (Na$_2$SO$_4$), concentrated and the crude product recrystallized from 2:1 water/isopropanol then dried over P$_2$O$_5$ in vacuo to provide N-2-nitrophenylsulfonyl aminoacid methyl ester I-2 as colorless crystals. To a 0° C. solution of N-2-nitrophenylsulfonyl aminoacid methyl ester I-2 (28 mmol), an alcohol R$_1$OH (25 mmol) and triphenylphosphine (28 mmol) in THF (10 mL) is slowly added DIAD (28 mmol) over 5 minutes. The reaction is allowed to warm to rt, then stirred additional 24 hours. The solvent is removed and the crude product purified on silica gel (Merck 60; hexanes/DCM/THF 12:6:1) to afford N-2-nitrophenylsulfonyl-N-alkyl-aminoacid methyl ester I-3.

Step 3
To a stirred suspension of N-2-nitrophenylsulfonyl-N-alkyl-aminoacid methyl ester I-3 (R$_2$=2-cyclopentylethyl, 11 mmol) and polymer bound 1,3,4,6,7,8-hexahydro-2H-pyrimidino[1,2-a]pyrimidine (12 mmol) in DMF (40 mL) is added thiophenol (22 mmol). After 1 hour, the reaction mixture is diluted with ether (300 mL), filtered and the filtrate washed with brine (5×50 mL) and saturated NaHCO$_3$ (50 mL). The combined basic aqueous washes are then back extracted with DCM (2×50 mL) and the DCM layers combined. The ether phase is then extracted with 0.5 M HCl (5×25 mL), the aqueous extract is made basic with solid NaHCO$_3$, then saturated with NaCl and extracted with (5×50 mL) DCM. All DCM layers are combined, dried (Na$_2$SO$_4$), acidified with 4 N HCl in dioxane and evaporated to provide the secondary amine hydrochloride salt I-4. In a separate flask, phosgene (20% in toluene; 0.11 mol) is added to a vigorously stirred 0° C. suspension of NaHCO$_3$ (1 mole) in water (125 mL) and ether (200 mL). To this is added dropwise over 30 min. the secondary amine HCl salt in water (125 mL) and an additional aliquot of phosgene (0.11 mol). The reaction mixture is allowed to warm to rt then stirred additional 15 minutes. The phases are separated and the organic phase washed with 1 M HCl (2×75 mL), brine (75 mL), dried (MgSO₄), and evaporated to provide N-alkyl-aminoacid methyl ester carbamoyl chloride I-5 (2 steps).

Step 4

An aliquot of N-alkyl-aminoacid methyl ester carbamoyl chloride I-5 (4 mmol) dissolved in DCM (4 mL) is added to a 0° C. solution of amine A-5 (5.3 mmol) in pyridine (4 mL). After 30 minutes, the reaction mixture is diluted with ether (100 mL), washed with 10% KHSO₄ (2×25 mL), brine (25 mL), dried (NaSO₄) and evaporated to provide the desired urea I-6.

To N-[(2-carboxypyrrolidin-1-carbonyl)amino] aminoacid methyl ester I-6 (200 μmol) in dioxane (2 mL). The solution is diluted with 50% aqueous hydroxylamine (1 mL), and the reaction stirred for 24–36 hours. The crude reaction mixture is then purified by preparative reverse-phase (C18) HPLC to afford N-hydroxy-2-[(2-amidopyrrolidin)amino]acetamide 1–7.

General Procedure J

Synthesis of 1-[2-S-(oxazol-2-yl)-pyrrolidin-1-yl]-2-R/S-mercaptomethyl-alkan-1-one

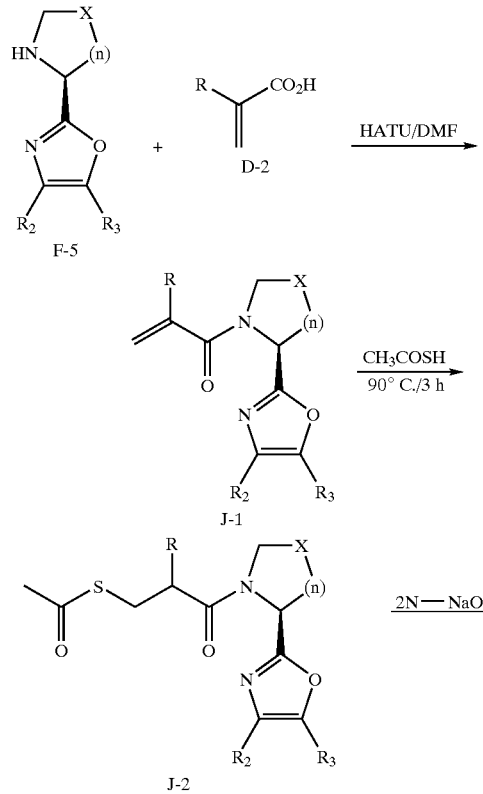

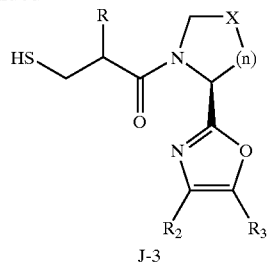

Step 1: 2-butyl-1-(2-S-oxazol-2-yl-pyrrolidin-1-yl)-propenone

To a solution of 2-butyl acrylic acid D-2 (1.2 mmol) in DMF (10 mL) is added bicyclic pyrrolidine F-5 (1.2 mmol), HATU (1.2 mmol) and DIEA (2.5 mmol). The mixture is stirred overnight, then concentrated and purified on silica gel (EtOAc/hexane 1:4) to afford of the desired amide J-1.

Step 2: Thiolacetic acid S-{2-R/S-[2-S-(oxazol-2-yl)-pyrrolidine-1-carbonyl]-hexyl} ester A solution of J-1 (3 mmol) in thiolacetic acid (15 mL) is heated at 90° C. for 3 hours then cooled to rt. It is diluted with EtOAc and washed with saline, cold aq. NaHCO₃, dried over Na₂SO₄ and concentrated under reduced pressure. The residue is purified on silica gel column using solvent gradient consisting of 5–20% acetone in DCM to afford J-2.

Step 3: 1-[2-S-(5-tert-butyl-oxazole-2-yl)-pyrrolidin-1-yl]-2-R/S-mercaptomethyl-hexan-1-one J-2 (1 mmol) is dissolved in MeOH (5 mL) under Argon with stirring. Degassed 2 M NaOH solution (6 mmol) is added, and the mixture is stirred for 3 hours. The reaction mixture is acidified with IR-120(H+) resin until pH 2. The resin is removed by filtration and filtrate is concentrated under reduced pressure to give the title J-3 as a clear oil.

General Procedure K

Synthesis of 2-S-hydroxy-3-R-(2-S-oxazol-2-yl-pyrrolidine-1-carbonyl)-alkanoic acid

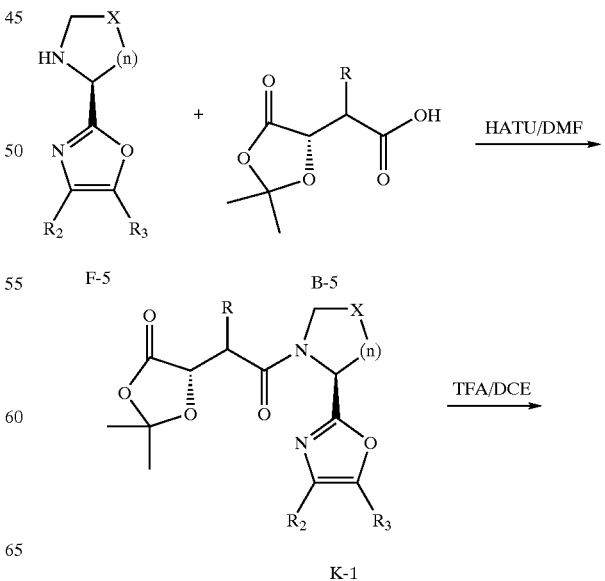

-continued

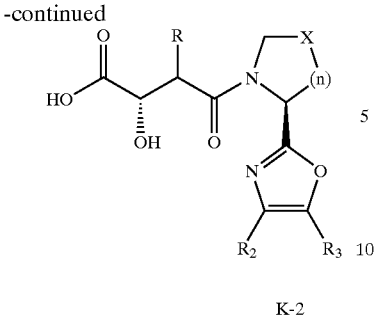

K-2

Step 1: 5-R-{1-[2-S-(5-tert-butyl-oxazol-2-yl)-pyrrolidine-1-carbonyl]-pentyl}-2,2-dimethyl-[1,3]dioxolan-4-one To a DMF solution (7 mL) of bicyclic amine salt (0.852 g, 2.4 mmol, 1.1 equiv) Hunig's base (2.1 mL, 12 mmol, 5.5 equiv.) is added and the mixture cooled to 0° C. This is followed by the addition of the acetonide (500 mg, 2.17 mmol, 1.0 equiv.), and HATU (0.913 g, 2.4 mmol, 1.1 equiv.) at 0° C. The resulting mixture is stirred at rt for 16 hours. The mixture is partitioned between excess EtOAc and 10% citric acid. The organic layer is washed with brine and saturated $NaHCO_3$, dried over anhydrous $Na_2SO_4$, filtered and concentrated to give K-1. The residue is carried forward as is to the final step.

ES-MS: calcd. for $C_{22}H_{34}N_2O_5$ (406.25); found: 407.5 [M+H].

Step 2: 3-R-[2-S-(5-tert-butyl-oxazol-2-yl)-pyrrolidine-1-carbonyl]-2-S-hydroxy-heptanoic acid The acetonide K-1 is dissolved in 10% (95:5 $TFA:H_2O$)/DCE (10 mL) and the reaction stirred at rt for 7 hours. The final product is purified by preparative HPLC which upon lyophylization yielded a final compound K-2 as a colorless powder.

The following examples are to illustrate the invention but should not be interpreted as a limitation thereon.

EXAMPLE 1
2(S)-hydroxy-3(R)-[2(R/S)-pyridin-2-yl-pyrrolidine-1-carbonyl)-heptanoic acid hydroxamide

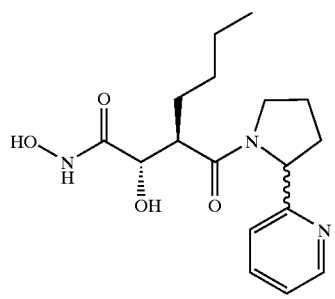

The title compound is prepared from 2-(2,2-dimethyl-4-oxo-1,3-dioxolan-5-yl)hexanoic acid B-5 and commercially available 2-pyrrolidin-2-yl-pyridine A-5 according to General Procedure B.

1H NMR (DMSO): δ 8.6–8.5 (m, 1H), 7.97–7.92 (t, J=7.4 & 7.1 Hz, 1H), 7.5–7.3 (m, 2H), 5.14–4.94 (m, 1H), 3.96–3.44 (m, 3H), 3.1–2.9 (m, 1H), 2.3–1.9 (m, 6H), 1.3–1.1 (m, 4H), 0.87–0.9 (m, 3H). ES-MS: calcd. for $C_{17}H_{25}N_3O_4$ (335.40); found: 336.5 [M+1].

EXAMPLE 2
2(S)-hydroxy-3(R)-[3(R/S)-pyridin-2-yl-pyrrolidine-1-carbonyl)-heptanoic acid hydroxamide

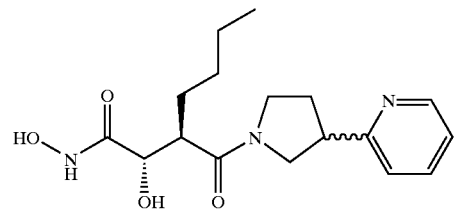

The title compound is prepared from 2-(2,2-dimethyl-4-oxo-1,3-dioxolan-5-yl)hexanoic acid B-5 and commercially available 2-pyrrolidin-3-yl-pyridine A-5 according to General Procedure B.

1H NMR (DMSO): δ 8.85–8.8 (m, 1H), 8.21–8.14 (m, 2H), 7.8–7.6 (m, 4H), 4.4–3.9 (m, 4H), 3.8–3.6 (m, 2H), 3.09–3.06 (d, J=9.34 Hz, 1H), 2.5–2.2 (m, 2H), 1.63 (bs, 2H), 1.38 (bs, 4H), 1.06–0.96 (m, 3H). ES-MS: calcd. for $C_{17}H_{25}N_3O_4$ (335.40); found: 336.5 [M+1].

EXAMPLE 3
2(S)-hydroxy-3(R)-[2-pyridin-3-yl-pyrrolidine-1-carbonyl)-heptanoic acid hydroxamide (Isomer 1)

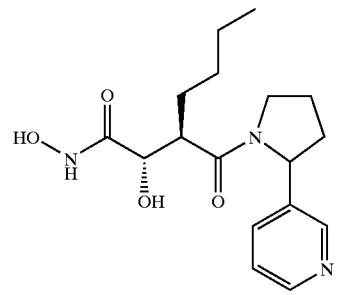

The title compound is prepared from 2-(2,2-dimethyl-4-oxo-1,3-dioxolan-5-yl)hexanoic acid B-5 and commercially available 3-pyrrolidin-2-yl-pyridine A-5 according to General Procedure B.

1H NMR (DMSO): δ 8.61 (s, 2H), 7.99–7.97 (d, J=7.97 Hz, 1H), 7.67–7.63 (m, 1H), 5.11–5.07 (m, 1H), 4.02–3.57 (m, 3H), 2.99–2.93 (m, 1H), 2.49–2.24 (m, 2H), 1.96–1.76 (m, 4H), 1.37–1.0 (m, 4H), −0.98–0.78 (m, 3H). ES-MS: calcd. for $C_{17}H_{25}N_3O_4$ (335.40); found: 336.5 [M+1].

EXAMPLE 4
2(S)-hydroxy-3(R)-[2-pyridin-3-yl-pyrrolidine-1-carbonyl)-heptanoic acid hydroxamide (Isomer 2)

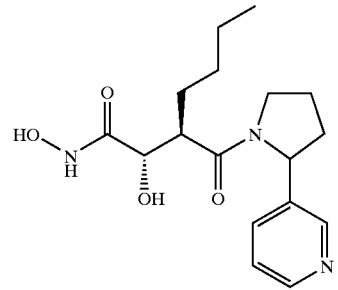

The title compound is the other isomer isolated from the reaction as described in Example 3.

1H NMR (DMSO): δ 8.86–8.76 (m, 2H), 8.32–8.3 (d, J=7.97 Hz, 1H), 7.9–7.88 (m, 1H), 5.4–5.32 (m, 1H), 4.3–3.74 (m, 3H), 3.22–3.16 (t, J=9.34 Hz, 1H), 2.52–2.46 (m, 2H), 2.26–1.98 (m, 3H), 1.63–1.38 (m, 5H), 1.07–1.01 (m, 3H). ES-MS: calcd. for $C_{17}H_{25}N_3O_4$ (335.40); found: 336.5 [M+1].

EXAMPLE 5

2(S)-hydroxy-3(R)-[2-pyridin-4-yl-pyrrolidine-1-carbonyl)-heptanoic acid hydroxamide (Isomer 1)

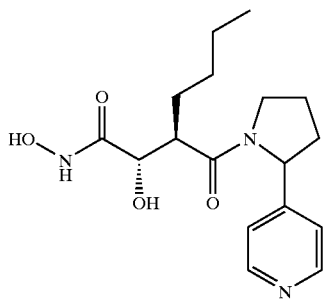

The title compound is prepared from 2-(2,2-dimethyl-4-oxo-1,3-dioxolan-5-yl)hexanoic acid B-5 and commercially available 4-pyrrolidin-2-yl-pyridine A-5 according to General Procedure B.

1H NMR (DMSO): δ 8.89–8.87 (d, J=4.7 Hz, 2H), 7.77–7.75 (d, J=5.8 Hz, 2H), 5.3–5.25 (m, 1H), 4.23–3.8 (m, 3H), 3.33–3.15 (m, 1H), 2.52–2.43 (m, 2H), 2.13–1.86 (m, 3H), 1.56–1.26 (m, 5H), 1.07–1.05 (m, 3H). ES-MS: calcd. for $C_{17}H_{25}N_3O_4$ (335.40); found: 336.5 [M+1].

EXAMPLE 6

2(S)-hydroxy-3(R)-[2-pyridin-4-yl-pyrrolidine-1-carbonyl)-heptanoic acid hydroxamide (Isomer 2)

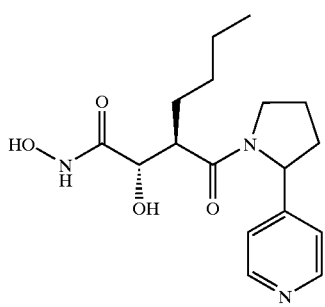

The title compound is the other isomer isolated from the reaction as described in Example 5.

1H NMR (DMSO): δ 8.89–8.85 (t, J=6.32 & 6.6 Hz, 2H), 7.92–7.68 (m, 2H), 5.39–5.36 (dd, 1H), 4.25–3.8 (m, 3H), 3.25–3.2 (t, J=7.96 & 8.8 Hz, 1H), 2.56–2.47 (m, 2H), 2.12–1.62 (m, 3H), 1.46–1.38 (m, 5H), 1.07–1.01 (m, 3H). ES-MS: calcd. for $C_{17}H_{25}N_3O_4$ (335.40); found: 336.5 [M+1].

EXAMPLE 7

2(S)-hydroxy-3(R)-[3(R/S)-pyridine-4-yl-pyrrolidine-1-carbonyl)-heptanoic acid hydroxamide

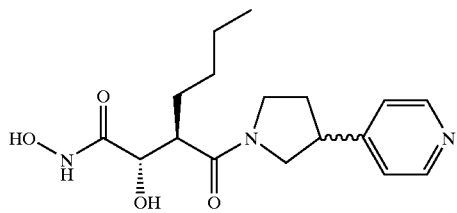

The title compound is prepared from 2-(2,2-dimethyl-4-oxo-1,3-dioxolan-5-yl)hexanoic acid B-5 and commercially available 4-pyrrolidin-3-yl-pyridine A-5 according to General Procedure B.

1H NMR (DMSO): δ 8.94 (dd, 2H), 8.06–8.02 (t, J=4.12 & 6.32 Hz, 2H), 4.2–3.53 (m, 6H), 3.1–3.02 (dd, 1H), 2.7–2.1 (m, 2H), 1.66–1.28 (m, 6H), 1.05–0.96 (m, 3H). ES-MS: calcd. for $C_{17}H_{25}N_3O_4$ (335.40); found: 336.5 [M+1].

EXAMPLE 8

2(S)-hydroxy-3(R)-[2(R/S)-phenyl-pyrrolidine-1-carbonyl)-heptanoic acid hydroxamide

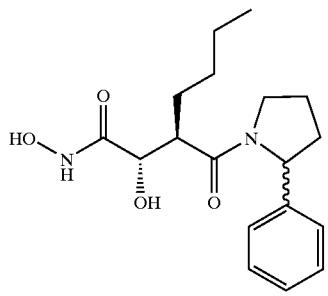

The title compound is prepared from 2-(2,2-dimethyl-4-oxo-1,3-dioxolan-5-yl)hexanoic acid A-5 and commercially available 2-phenyl-pyrrolidine B-5 according to General Procedure B.

1H NMR (DMSO): δ 7.6–7.3 (m, 5H), 5.6–5.57 (d, J=7.14 Hz, 1H), 5.3–5.24 (m, 1H), 4.21–3.72 (m, 4H), 3.2–3.14 (t, J=7.96 & 10.44 Hz, 1H), 2.4–2.33 (m, 1H), 2.3–1.85 (m, 4H), 1.6–1.36 (m, 5H), 1.04–0.97 (m, 3H). ES-MS: calcd. for $C_{18}H_{26}N_2O_4$ (334.42); found: 335.5 [M+1].

EXAMPLE 9

2(S)-hydroxy-3(R)-[3(R/S)-phenyl-pyrrolidine-1-carbonyl)-heptanoic acid hydroxamide

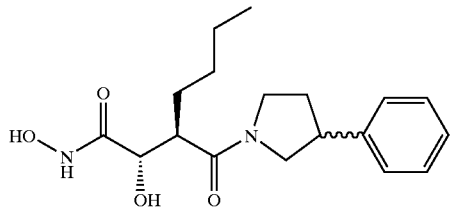

The title compound is prepared from 2-(2,2-dimethyl-4-oxo-1,3-dioxolan-5-yl)hexanoic acid B-5 and commercially available 3-phenyl-pyrrolidine A-5 according to General Procedure B.

1H NMR (DMSO): δ 7.56–7.4 (m, 5H), 4.4–3.4 (m, =6H), 3.09–3.08 (d, J=3.85 Hz, 1H), 2.49–1.97 (m, 3H), 1.64–1.34 (m, 5H), 1.05–1.02 (m, 3H). ES-MS: calcd. for $C_{18}H_{26}N_2O_4$ (334.42); found: 335.5 [M+1].

EXAMPLE 10

2(S)-hydroxy-3(R)-[3(R/S)-pyridin-3-yl-pyrrolidine-1-carbonyl)-heptanoic acid hydroxamide

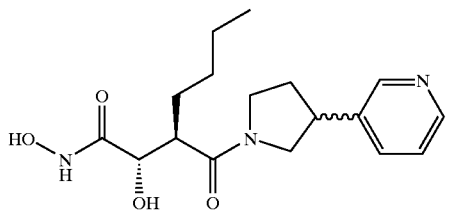

The title compound is prepared from 2-(2,2-dimethyl-4-oxo-1,3-dioxolan-5-yl)hexanoic acid B-5 and commercially available 3-pyrrolidin-3-yl-pyridine A-5 according to General Procedure B.

1H NMR (DMSO): δ 8.89–8.76 (m, 2H), 8.26–8.2 (m, 1H), 7.79–7.74 (t, J=4.7 & 7.7 Hz, 1H), 4.1–3.5 (m, 6H), 3.09–3.07 (d, J=7.42 Hz, 1H), 2.54–1.37 (m, 8H), 1.05–0.97 (m, 3H). ES-MS: calcd. for $C_{17}H_{25}N_3O_4$ (335.40); found: 336.5 [M+1].

EXAMPLE 11

2(S)-hydroxy-3(R)-[2(S)-oxazol-2-yl-pyrrolidine-1-carbonyl)-heptanoic acid hydroxamide

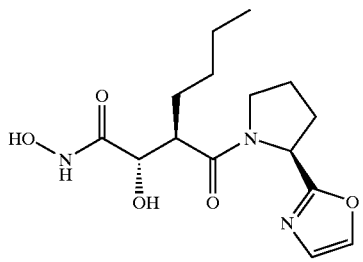

The title compound is prepared from 2-(2,2-dimethyl-4-oxo-1,3-dioxolan-5-yl)hexanoic acid B-5 and 2-(S)-pyrrolidin-2-yl-oxazole A-5 (synthesis is described in Procedure E) according to General Procedure B.

1H NMR (CDCl$_3$): δ 7.8 (s, 1H), 7.3 (s, 1H), 5.45–5.43 (t, J=3.9 & 3.8 Hz, 1H), 4.45 (d, J=2.5 Hz, 1H), 4.1–3.96 (m, 2H), 3.54–3.51 (t, J=5.5 & 2.2 Hz, 1H), 2.5–2.3 (m, 4H), 1.95–1.91 (m, 2H), 1.57–1.53 (m, 4H), 1.12–1.08 (t, J=6.04 & 7.14 Hz, 3H). ES-MS: calcd. for $C_{15}H_{23}N_3O_5$ (325.36); found: 326.4 [M+1].

EXAMPLE 12

2(S)-hydroxy-3(R)-[2(S)-(5-methyl-oxazol-2-yl-pyrrolidine-1-carbonyl)-heptanoic acid hydroxamide

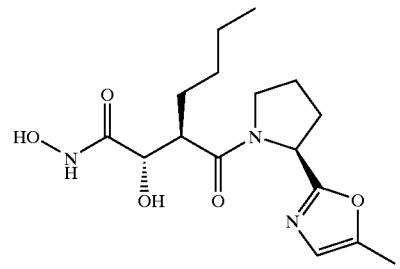

The title compound is prepared from 2-(2,2-dimethyl-4-oxo-1,3-dioxolan-5-yl)hexanoic acid and 5-methyl-2-(S)-pyrrolidin-2-yl-oxazole F-5 ($R^1$=H, $R_2$=CH$_3$; preparation is described in Procedure F) according to General Procedure B.

1H NMR (CDCl$_3$): δ 7.46 (s, 1H), 5.36–5.33 (m, 1H), 4.45–4.42 (m, 1H), 4.15–3.91 (m, 2H), 3.58–3.40 (m, 1H), 2.46(s,3H), 2.40–2.21 (m, 4H), 1.93–1.83 (m, 2H), 1.51–1.49 (m, 4H), 1.08 (t, J=6.9 Hz, 3H). ES-MS: calcd. for $C_{16}H_{25}N_3O_5$ (339.39); found: 340.6 [M+1].

EXAMPLE 13

2(R)-fluoro-3-(R)-(2-S-oxazol-2-yl-pyrrolidine-1-carbonyl)-heptanoic acid hydroxamide

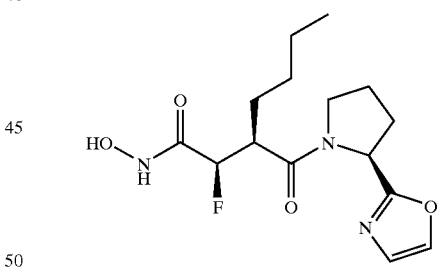

The title compound is prepared according to General Procedure C 2-(2,2-dimethyl-4-oxo-1,3-dioxolan-5-yl) hexanoic acid B-5 is coupled with 5-methyl-2-(S)-pyrrolidine-2-yl-oxazole A-5 (prepared as described in Procedure E) to give B-6 which is then treated further as described in Procedure C to afford the title compound as one of the isomer.

1H NMR (DMSO): δ 8.16 (s, 1H), 7.3 (s, 1H), 5.22–5.18 (dd, 1H), 5.07–4.9 (dd, J=7.97 & 8.24 Hz, 1H), 3.9–3.65 (m, 2H), 3.4–3.35 (m, 1H), 2.37–2.07 (m, 4H), 1.78–1.76 (d, J=6.04 Hz, 2H), 1.42 (bs, 4H), 1.03 (bs, 3H). ES-MS: calcd. for $C_{15}H_{22}FN_3O_4$ (327.56); found; 350.5 [M+23].

EXAMPLE 14
2(S)-fluoro-3-(R)-(2-S-oxazol-2-yl-pyrrolidine-1-carbonyl)-heptanoic acid hydroxamide

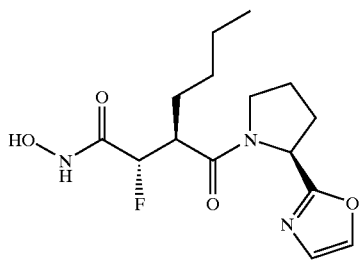

The title compound is the other isomer isolated from the reaction as described in Example 13.

1H NMR (DMSO): δ 8.16 (s,1H), 7.3 (s, 1H), 5.33–5.29 (dd, 1H), 4.97–4.78 (dd, J=9.89 & 10.44 Hz, 1H), 3.94–3.7 (m, 2H), 3.38–3.32 (m, 1H), 2.42–2.08 (m, 6H), 1.54–1.38 (m, 4H), 1.02–0.99 (m, 3H). ES-MS: calcd. for $C_{15}H_{22}FN_3O_4$ (327.56); found: 328.5 [M+1].

EXAMPLE 15
N-hydroxy-N-[2-(2-oxazol-2-yl-pyrrolidine-1-carbonyl)-hexyl]-formamide

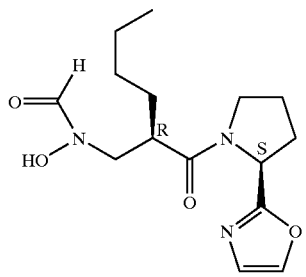

The title compound is prepared from 2-[(benzyloxy-formyl-amino)-methyl]-hexanoic acid D-7 (R=n-butyl) and 2-(S)-pyrrolidine-2-yl-oxazole E-5 (prepared as described in Procedure E) according to General Procedure D.

1H NMR (DMSO-$d_6$): δ 9.89 (s, 1H), 8.16 (s, 1H), 7.97 (s, 1H), 7.29 (s, 1H), 5.28–5.21 (m, 1H), 3.88–3.45 (m, 4H), 3.31–3.02 (m, 1H), 2.41–2.27 (m, 1H), 2.20–2.03 (m, 4H), 1.57–1.41 (m, 5H), 1.02 (bs, 3H). ES-MS: calcd. for $C_{15}H_{23}N_3O_4$ (309.36); found: 310.6 [M+H], 332.5 M+Na].

EXAMPLE 16
N-hydroxy-N-[3(R)-(2-R/S-pyridin-2-yl-pyrrolidine-1-carbonyl)-hexyl]-formamide (Isomer 1)

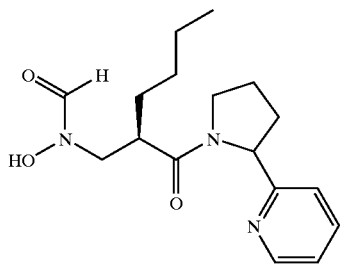

The title compound is prepared from 2-[(benzyloxy-formyl-amino)-methyl]-hexanoic acid D-7 (R=n-butyl) and commercially available 2-pyrrolidin-2-yl-pyridine A-5 according to General Procedure D.

1H NMR ($D_2O$): δ 8.55 (d, J=4.9, 1H), 7.99–7.96 (m, 1H), 7.78 (s, 1H), 7.37–7.28 (m, 2H), 5.02 (dd, J=3.6, 3.6, 1H), 3.80–3.63 (m, 1H), 3.61–3.52 (m, 1H), 3.32–3.25 (m, 1H), 2.37–2.09 (m, 1H), 1.98–1.85 (m, 2H), 1.48–1.35 (m, 1H), 1.36–1.19 (m, 4H), 0.85–0.81 (t, J=11.8, 3H). ES-MS: calcd. for $C_{18}H_{27}N_5O_4$ (319.2); found: 320.5 [M+H].

EXAMPLE 17
N-hydroxy-N-[3(R)-(2-R/S-pyridin-2-yl-pyrrolidine-1-carbonyl)-hexyl]-formamide (Isomer 2)

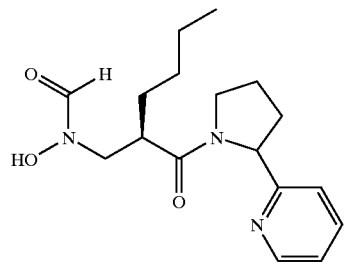

The title compound is the other isomer isolated from the reaction as described in Example 16.

1H NMR ($D_2O$): δ 8.59 (d, J=5.8, 1H), 8.41 (dd, J=7.7, 7.7 1H), 7.82–7.75 (m, 1H), 7.59 (s, 1H), 7.56–7.49 (m, 1H), 5.22 (dd, J=4.7, 8.8, 1H), 4.05–3.89 (m, 1H), 3.87–3.80 (m, 1H), 3.72–3.62 (m, 1H), 3.54 (dd, J=3.9, 14.8, 1H), 3.41–3.28 (m, 1H), 2.53–2.44 (m, 2H), 2.12–1.94 (m, 4H), 1.80–1.45 (m, 2H), 1.40–1.23 (m, 4H), 0.89 (dd, J=5.5, 6.9, 3H). ES-MS: calcd. for $C_{18}H_{27}N_5O_4$ (319.2); found: 320.5 [M+H].

EXAMPLE 18
2(S)-hydroxy-3(R)-[2-S-(4,5-dimethyl-thiaazol-2-yl-pyrrolidine-1-carbonyl]-heptanoic acid hydroxamide

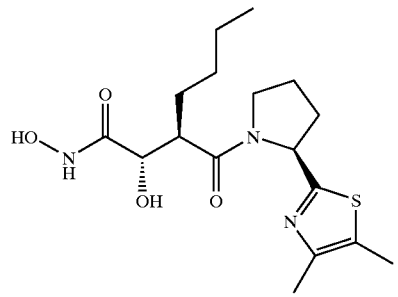

The title compound is prepared from 2-(2,2-dimethyl-4-oxo-1,3-dioxolan-5-yl)hexanoic acid B-5 and 2-(S)-pyrrolidin-2-yl-(4,5-dimethyl-thiaazole) G-4 ($R_2=R_3=CH_3$, synthesis is described in Procedure G) according to General Procedure B.

1H NMR ($CDCl_3$): δ 5.41–5.37 (dd, J=2.5 Hz, 1H), 4.04–4.01 (m, 1H), 3.97 (d, J=9 Hz, 1H), 3.85–3.78 (m, 1H), 3.14–3.08 (m, 1H), 2.44 & 2.39 (each s, 2×3H), 2.32–2.11 (m,4H), 1.61–1.39 (m, 6H), 1.03 (t, J=6.0 Hz, 3H). ES-MS: calcd. for $C_{17}H_{27}N_3O_4S$ (369.17); found: 370.3 [M+1].

EXAMPLE 19

Synthesis of 2(S)-hydroxy-3(R)-[2-S-(4-phenyl-thiaazol-2-yl-pyrrolidine-1-carbonyl]-heptanoic acid hydroxamide

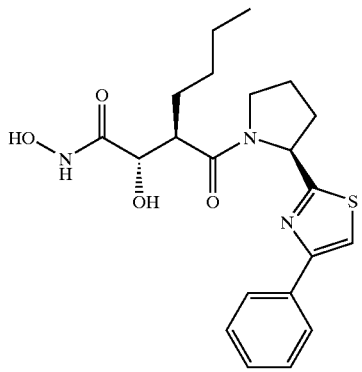

The title compound is prepared from 2-(2,2-dimethyl-4-oxo-1,3-dioxolan-5-yl)hexanoic acid B-5 and 2-(S)-pyrrolidin-2-yl-(4-phenyl-thiaazole) G-4 ($R_2=C_6H_5$, $R_3=H$, synthesis is described in Procedure G) according to General Procedure B.

1H NMR (CDCl$_3$): δ 8.18–8.10 (m, 3H), 7.64–7.49 (m, 3H), 5.59–5.58 (dd, J=2.8 Hz, 1H), 4.10–4.01 (m, 1H), 3.95 (d, J=7 Hz, 1H), 3.91–3.89 (m, 1H), 3.18–3.14 (m, 1H), 2.41–2.19 (m, 4H), 1.64–1.37 (m, 6H), 1.01(t, J=6.0 Hz, 3H). ES-MS: calcd. for $C_{21}H_{27}N_3O_4S$ (417.52); found: 418.5 [M+1].

EXAMPLE 20

2(S)-hydroxy-3(R)-[2-S-(4-methyl-thiaazol-2-yl-pyrrolidine-1-carbonyl]-heptanoic acid hydroxamide

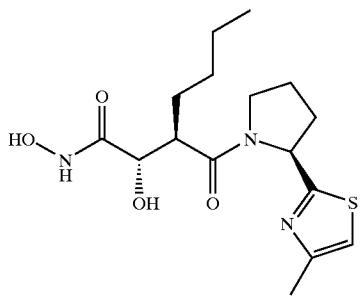

The title compound is prepared from 2-(2,2-dimethyl-4-oxo-1,3-dioxolan-5-yl)hexanoic acid B-5 and 2-(S)-pyrrolidin-2-yl-(4-methyl-thiaazole) G-4 ($R_2=CH_3$, $R_3=H$, preparation is described in Procedure G) according to General Procedure B.

1H NMR (CDCl$_3$): δ 7.49–7.6 (dd, 1H), 7.05 (bs, 1H), 5.71–5.69 (d, J=6.04 Hz, 1H), 4.45 (bs, 1H), 4.08–3.94 (d, 2H), 3.51 (bs, 1H), 2.67–2.63 (t, 3H), 2.3 9bs, 4H), 1.96 (bs, 2H), 1.57 (bs, 4H), 1.12–1.10 (d, 3H). ES-MS: calcd. for $C_{16}H_{25}N_3O_4S$ (355.47); found: 356.3 [M+1].

EXAMPLE 21

2(S)-hydroxy-3(R)-[2-S-(benzimidazol-2-yl-pyrrolidine-1-carbonyl]-heptanoic acid hydroxamide

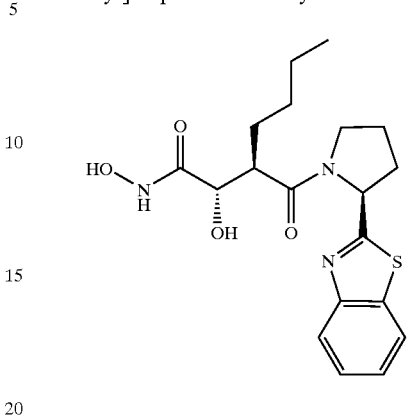

The title compound is prepared from 2-(2,2-dimethyl-4-oxo-1,3-dioxolan-5-yl)hexanoic acid B-5 and 2-(S)-pyrrolidin-2-yl-(benzimidazole) G-4 (synthesis is described in Procedure G) according to General Procedure B.

1H NMR (DMSO): δ 7.78–7.66 (m, 2H), 7.51–7.37 (m, 2H), 5.41–5.37 (m, 1H), 5.25–5.21 (t, J=6.32 Hz, 1H), 3.8–3.52 (m, 2H), 3.02–2.9 (m, 1H), 2.38–2.06 (m, 4H), 1.47–1.03 (m, 6H), 0.87–0.70 (m, 3H). ES-MS: calcd. for $C_{19}H_{26}N_4O_4$ (374.44); found: 375.3 [M+1].

EXAMPLE 22

N-hydroxy-2-[N-(2-cyclopentylethyl)-N)-[2-S-(4-phenyl)-thiaazol-2-yl-pyrrolidine]-acetamide The title compound is prepared from I-5 and 2-(S)-pyrrolidin-2-yl-(5-phenyl-thiaazole) G-4 ($R_2=C_6H_5$, $R_3=H$) according to General Procedure I-4.

1H NMR (D$_6$ DMSO): δ 7.93–7.91 (m, 3H), 8.41 (dd, J=7.1, 7.1 2H), 7.35–7.30 (m, 1H), 5.31 (dd, J=6.9, 6.9 1H), 3.89 (d, J=16.2 1H), 3.62 (d, J=16.2 1H), 3.58–3.40 (m, 2H), 3.30–3.15 (m, 2H), 2.42–2.39 (m, 1H), 1.96–1.83 (m, 3H), 1.69–1.60 (m, 3H), 1.54–1.43 (m, 6H), 1.07–0.96 (m, 2H). ES-MS: calcd. for $C_{23}H_{30}N_4O_3S$ (442.2); found: 465.3 [+Na].

EXAMPLE 23

N-hydroxy-2-[N-(2-cyclopentylethyl)-N-[2-(2-oxazol-2-yl-pyrrolidine-1-carbonyl)-hexyl]-acetamide The title compound is prepared from I-5 and 5-methyl-2-(S)-pyrrolidine-2-yl-oxazole E-5 (prepared as described in Procedure E) according to General Procedure I-4.

1H NMR (D$_6$ DMSO): δ 7.97 (s, 1H), 7.09 (s, 1H), 5.07 (dd, J=7.1, 7.1 1H), 3.81 (d, J=16.2 1H), 3.47–3.39 (m, 2H), 3.25–2.99 (m, 2H), 2.26–2.22 (m, 1H), 1.98–1.81 (m, 3H), 1.69–1.60 (m, 3H), 1.78–1.42 (m, 7H), 1.04–1.02 (m, 2H). ES-MS: calcd. for $C_{17}H_{26}N_4O_4$ (350.2); found: 373.4 [M+Na].

EXAMPLE 24

2(S)-hydroxy-3(R)-[2(S)-(5-tert-butyl-oxazol-2-yl-pyrrolidine-1-carbonyl)-heptanoic acid hydroxamide

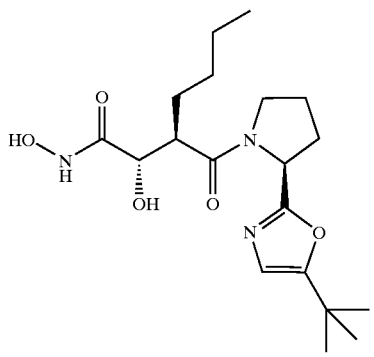

The title compound is prepared from 2-(2,2-dimethyl-4-oxo-1,3-dioxolan-5-yl)hexanoic acid and 5-tert-butyl-2-(S)-pyrrolidin-2-yl-oxazole F-5 (R$^1$=H, R$_2$=tert-butyl) according to General Procedure B.

1H NMR (DMSO): δ 6.87–6.85 (d, J=5.22 Hz, 1H), 5.25–5.21 (dd, J=3.02 & 2.74 Hz, 1H), 4.04–3.96 (m, 2H), 3.86–3.79 (m, 1H), 3.13–3.07 (t, J=9.06 & 9.9 1 Hz), 2.35–2.28 (m, 2H), 2.26–2.05 (m, 2H), 1.59–1.37 (m, 6H), 1.013–0.997 (t, J=4.8 & 6.32 Hz,3H). ES-MS: calcd. for $C_{19}H_{31}N_3O_5$ (381.47); found: 382.4 [M+H].

5-tert-butyl-2-(S)-pyrrolidine-2-yl-oxazole is prepared as described:

1-amino-pinacolone

To a solution of 1-bromo-pinacolone (5.4 g, 1 equiv.) in DMF (30 mL) is added sodium azide (4 g, 5 equiv.) at 0° C., stirred at 0° C. for 1 hour and then brought to rt for 1 hour. The reaction mixture is diluted with EtOAc (150 mL) and washed with cold water, dried over sodium sulfate. This azido compound is treated with 10% Pd—C in ethanol-conc HCl to give corresponding the title compound.

5-tert-butyl-2-S-pyrrolidine-2-yl-oxazole

A solution of Z-L-Pro chloride (1 equiv.) in DCM is treated with 1-amino-pinacolone (1.2 equiv.) in pyridine at rt for 5 hours. After usual work up, the resulting amide intermediate is treated with POCl$_3$ at 70° C. for 2 hours to provide the Z-N-protected bicyclic compound. Treatment with HBr—AcOH affords title compound.

1H NMR (DMSO): δ 9.51 (bs, 1H), 5.04 (bs, 1H), 3.49 (bs, 2H), 2.54–2.21 (m, 4H), 1.45 (bs, 9H). ES-MS: calcd. for $C_{11}H_{18}N_2O$ (194.14); found: 195.3 [M+H]

EXAMPLE 25

2(S)-hydroxy-3(R)-[2(S)-(5-phenyl-oxazol-2-yl-pyrrolidine-1-carbonyl)-heptanoic acid hydroxamide

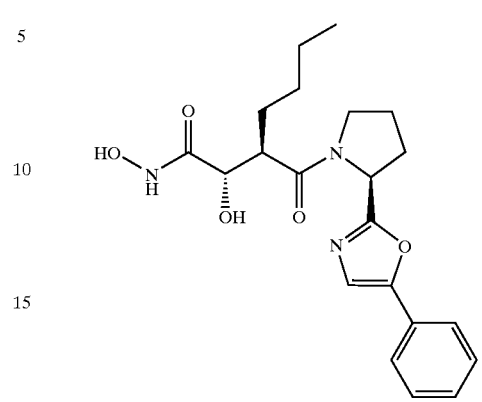

The title compound is prepared from 2-(2,2-dimethyl-4-oxo-1,3-dioxolan-5-yl)hexanoic acid and 5-phenyl-2-(S)-pyrrolidin-2-yl-oxazole F-5 (R$^1$=H, R$_2$=phenyl) according to General Procedure B.

1H NMR (DMSO): δ 7.86–7.83 (m, 1H), 7.77 (bs, 1H), 7.76–7.62 (m, 3H), 7.56–7.52 (m, 1H), 5.6–5.58 (d, J=6.32 Hz, 1H), 5.32–5.29 (d, J=6.59 Hz, 1H), 4.07–3.92 (m, 2H), 3.14–3.11 (m, 1H), 2.42–2.18 (m, 4H), 1.56–1.37 (m, 6H), 0.882 (bs, 3H). ES-MS: calcd. for $C_{21}H_{27}N_3O_5$ (401.46); found: 402.2 [M+H].

The amine is prepared following the same procedure as described in the Example 24 from 2-bromoacetophenone

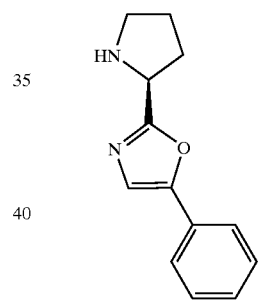

EXAMPLE 26

2(S)-hydroxy-3(R)-[2(S)-(5-iso-butyl-oxazol-2-yl-pyrrolidine-1-carbonyl)-heptanoic acid hydroxamide

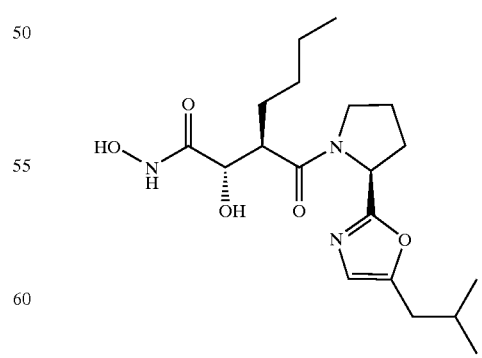

The title compound is prepared from 2-(2,2-dimethyl-4-oxo-1,3-dioxolan-5-yl)hexanoic acid and 5-iso-butyl-2-(S)-pyrrolidin-2-yl-oxazole F-5 (R$^1$=H, R$_2$=iso-butyl) according to General Procedure B.

1H NMR (DMSO):δ 6.93 (bs, 1H), 5.23–5.19 (dd, J=3.57 & 3.02 Hz, 1H), 4.05–3.95 (m, 2H), 3.83–3.78 (dd, J=6.87 & 7.14 Hz, 1H), 3.13–3.07 (t, J=9.34 & 8.42 Hz, 1H), 2.7–2.57 (m, 2H), 2.47–1.97 (m, 5H), 1.58–1.35 (m, 6H), 1.13–0.99 (m, 9H). ES-MS: calcd. for $C_{19}H_{31}N_3O_5$ (381.47); found: 382.3 [M+H]

Bromination of 4-methyl-2-butanone provided the desired bromo compound (major) along with other positional isomer in low yield. Amine is prepared from this bromide following the same procedure as described in the Example 24.

EXAMPLE 27
2(S)-hydroxy-3(R)-[2(S)-(4,5-dimethyl-oxazol-2-yl-pyrrolidine-1-carbonyl)-heptanoic acid hydroxamide

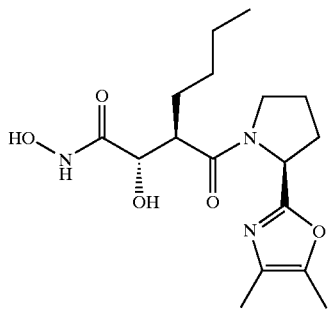

The title compound is prepared from 2-(2,2-di-methyl-4-oxo-1,3-dioxolan-5-yl)hexanoic acid and 4,5-di-methyl-2-(S)-pyrrolidin-2-yl-oxazole F-5 ($R^1$=Me, $R_2$=Me) according to General Procedure B.

1H NMR (DMSO): δ 5.17–5.13 (dd, J=3.57 & 3.02 Hz, 1H), 4.06–3.92 (m, 2H), 3.86–3.82 (dd, J=7.42 & 4.12 Hz, 1H), 3.12–3.06 (t, J=8.79 & 8.06 Hz, 1H), 2.56–2.26 (m, 2H), 2.35 (bs, 3H), 2.18–2.05 (m, 2H), 2.14 (bs, 3H), 1.57–1.35 (m, 6H), 1.04–1.02 (d, J=6.043 Hz, 3H). ES-MS: calcd. for $C_{17}H_{27}N_3O_5$ (353.41); found: 354.63 [M+H].

4,5-di-methyl-2-(S)-pyrrolidin-2-yl-oxazole is prepared as follows:
2-amino-butan-3-one To a solution of di-tert-butyl imino carboxylate (28 g, 1 equiv.) in DMF is added $Cs_2CO_3$ (134 g, 3 equiv.) and tetrabutylammonium iodide (154 g, 3 equiv.) under Argon atmosphere. After 1 hour, 2-chloro-butan-3-one (40 mL, 3 equiv.) is added to reaction mixture and the mixture stirred at rt for 72 hours, diluted with EtOAc and filtered through Celite to remove the inorganic material. The filtrate is washed with aq. $NaHCO_3$, water, 10% aq. citric acid, dried over $Na_2SO_4$ and concentrated under reduced pressure. The residue is purified on silica gel chromatography to give Boc protected compound. Treatment of this intermediate with 4 M HCl for 16 hours and evaporation of the solvent provides 2-amino-butan-3-one.
4,5-di-methyl-2-S-pyrrolidine-2-yl-oxazole

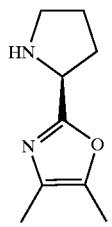

A solution of Z-L-Pro chloride (1 equiv.) in DCM is treated with 2-amino-butan-3-one (1.5 equiv.) in pyridine at rt for 5 hours. After usual work up, the resulting amide intermediate is treated with $POCl_3$ at 70° C. for 2 hours providing the Z-N-protected bicyclic intermediate. Treatment of this material with HBr—AcOH affords title compound.

1H NMR (DMSO): δ 4.99–4.94 (t, J=7.32 & 6.7 Hz, 1H), 3.49–3.42 (m, 2H), 2.56–2.1 (m, 10H). ES-MS: calcd. for $C_9H_{14}N_2O$ (166.11); found: 167.3 [M+H].

EXAMPLE 28
2-S-hydroxy-3-R-(2-S-oxazol-2-yl-pyrrolidine-1-carbonyl)-heptanoic acid

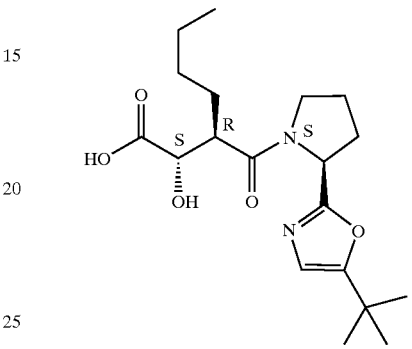

The title compound is prepared from 2-(2,2-dimethyl4-oxo-1,3-dioxolan-5-yl)hexanoic acid and 5-tert-butyl-2-(S)-pyrrolidin-2-yl-oxazole F-5 ($R^1$=H, $R_2$=tert-butyl) according to General Procedure K followed by the treatment with 90% aq. TFA-DCE.

1H NMR (DMSO): δ 6.48 (s, 1H), 5.21–5.18 (dd, J=3.65 & 3.3 Hz, 1H), 4.15–3.92 (m, 3H), 3.80–3.74 (m, 1H), 2.92–2.86 (m, 2H), 2.32–2.28 (m, 1H), 2.14–2.03 (m, 3H), 2.02–1.36 (m, 15H), 1.012–0.973 (t, J=6.6 & 5.22 Hz,3H). ES-MS: calcd. for $C_{19}H_{30}N_2O_5$ (366.46); found: 367.5 [M+H].

EXAMPLE 29
1-[2-S-(5-tert-butyl-oxazole-2-yl)-pyrrolidin-1-yl]-2-R/S-mercaptomethyl-hexan-1-one

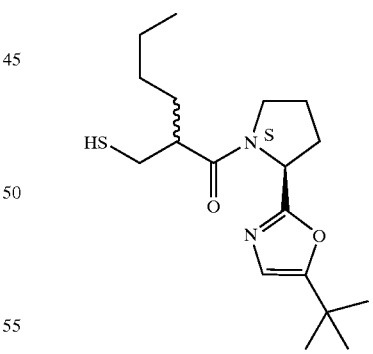

The title compound is prepared from 2-butyl acrylic acid (D-2) and 5-tert-butyl-2-(S)-pyrrolidin-2-yl-oxazole F-5 ($R^1$=H, $R_2$=tert-butyl) according to General Procedure J followed by the treatment with thiolacetic acid at 90° C. for 3 hours to give S-acetyl compound. The removal of acetyl group with 2N-sodium hydroxide in MeOH provided the isomeric mixture of title this compound.

1H NMR ($CDCl_3$): δ 6.62 (s, 0.6H), 6.55 (s, 0.4H), 4.09–4.04 (m, 0.6H), 3.72–3.74 (m, 2H), 3.62–3.53 (m, 0.4H), 2.95–2.73 (m, 2H), 2.61–2.40 (m, 0.6H), 2.38–2.30

(m, 0.4H), 2.27–2.00 (m, 6H), 1.71–1.64 (m, 4H), 1.56–1.44 (m, 1H, SH), 1.26 (bs, 9H), 0.89 (t, J=7Hz, 3H), 0.74 (t, J=7Hz, 3H). ES-MS: calcd. for $C_{18}H_{30}N_2O_2$ S (338.51); found: 339.5 [M+H].

Preferred compounds according to the invention are, e.g., the compounds of Examples 11–15.

The compounds of the invention, e.g., the compounds of formula (I), in free form or in pharmaceutically acceptable salt from or a prodrug thereof, exhibit valuable pharmacological properties, e.g., as anti-infectious agents, e.g., as indicated in in vitro and in vivo tests and are therefore indicated for therapy.

A. Inhibition of Peptide Deformylase Activity

The PDF/FDH coupled assay (see Lazennec et al., Anal. Biochem., Vol. 224, pp. 180–182 (1997)) is used. In this coupled assay, the formate released by PDF from its substrate fMAS is oxidized by the coupling enzyme FDH, reducing one molecule of $NAD^+$ to NADH, which causes an increase in absorption at 340 nM. All assays are carried out at rt in a buffer of 50 mM HEPES, pH 7.2, 10 mM NaCl, 0.2 mg/mL BSA, in half-area 96-well microtiter plates (Corning). The reaction is initiated by adding a mixture of 0.5 U/mL FDH, 1 mM $NAD^+$, and fMAS at the desired concentration. To determine $IC_{50}$ values, PDF is pre-incubated for 10 minutes with varying concentrations of actinonin, and the deformylation reaction is initiated by the addition of reaction mixture containing 4 mM fMAS. The initial reaction velocity, y, is measured as the initial rate of absorption increase at 340 nM using a SpectraMax plate reader (Molecular Devices, Sunnyvale, Calif.). The inhibitor concentration [In] at which 50% of the enzyme activity is inhibited, $IC_{50}$, is calculated using the following formula:

$$y=y_o/(1+[In]/IC_{50})$$

where $y_o$ is the reaction velocity in the absence of inhibitor. Solving this equation for $IC_{50}$ at the [In] when $y=y_o/2$ yields $IC_{50}$. The $IC_{50}$ is calculated based on a nonlinear least-square regression fit using a commercial software package (Deltapoint, Inc., Chicago, Ill.).

Using this assay, the $IC_{50}$ of various compounds are determined. The $IC_{50}$ for the various compounds is determined against deformylase enzyme containing nickel and zinc as the metal ion. The $IC_{50}$ values of preferred compounds of formula (I) determined for the zinc-containing deformylase ranged from about 0.585 $\mu M$ to about 0.004 $\mu M$. The $IC_{50}$ values of preferred compounds of formula (I) determined for the nickel-containing deformylase ranged from about 0.06 $\mu M$ to about 0.0001 $\mu M$.

B. Assay for Testing Antimicrobial Activity

Minimum inhibitory concentrations (MICs) are determined using the microdilution method in 96-well format plates. Compounds are suspended in DMSO at 5 or 10 mg/mL and stored at 4° C. until used. They are diluted in Mueller-Hinton Broth (MHB) or Trypticase Soy Broth (TSB) and used for MIC determination. The range of concentrations tested is 64–0.0625 $\mu g/mL$ final concentration using a two-fold dilution system.

The inoculum is prepared from cells grown on Trypticase Soy Agar (TSA) and incubated overnight at 35° C., 5–10 colonies are used to inoculate MHB or TSB broths, and the culture is incubated overnight at 35° C. The overnight culture is diluted 1:10, incubated for 1 hour at 35° C., diluted to the appropriate inoculum size and applied to the wells containing broth and test compound. Inoculum sizes are $2\times10^4$ CFU/mL.

Plates are incubated at 35° C. for 48 hours and MIC are recorded after 18 hours of incubation for bacteria. MIC is defined as the lowest concentration of compound that does not produce visible growth after incubation.

Minimum inhibitory concentration for various preferred compounds of formula (I) ranged from about 0.125 $\mu g/mL$ to about 2.0 $\mu g/mL$ against *H. influenza* (four strains), from about 0.25 $\mu g/mL$ to about greater than 64 $\mu g/mL$ against *S. aureus* (four strains), from about 2 $\mu g/mL$ to about 16 $\mu g/mL$ against *S. pneumonia* (three strains), and from about 0.125 $\mu g/mL$ to about 2 $\mu g/mL$ against *M. catarrhalis*. The deformylase enzyme is obtained from *E. coli*.

C. Demonstration of Selective Inhibition of PDF compared to MMP-7

As noted previously, inhibitors which are selective for PDF over MMPs are desirable in order to avoid side effects.

In order to test the compounds of the invention for possible inhibitory effects on MMPs, the following assay for MMP-7 is used.

MMP-7 assay

Matrilysin activity is assayed using a thio-peptide (Pro-Leu-Gly-S-Leu-Leu-Gly) as substrate. Upon enzyme hydrolysis, the thiolate is released as a product. The thiolate thus generated reacts with DTNB (dithionitrobenzene), giving rise to a yellow color which is monitored at 405 nM. The assay is carried out at rt; the assay buffer contains 50 mM Tricine, pH 7.5, 0.2 M NaCl, 10 mM $CaCl_2$, and 0.05% Brij, in a half-area 96-well microtiter plate. The reaction is initiated by adding a mixture of 200 TM DTNB and 100 TM thiopeptide in buffer. To determine $IC_{50}$ values, MMP-7 is pre-incubated for 10 minutes with varying concentrations of compounds, and the hydrolysis initiated by the addition of reaction mixture containing thiopeptide and DTNB. The reaction rate is recorded as the absorbance increase in $OD_{405}$ over 30 minutes using a SpectraMax plate reader (Molecular Devices, Sunnyvale, Calif.). The inhibitor concentration [In] at which 50% of the enzyme activity is inhibited, $IC_{50}$, is calculated using the following formula:

$$y=y_o/(1+[In]/IC_{50})$$

where $y_o$ is the reaction velocity in the absence of inhibitor. Solving this equation for $IC_{50}$ at the [In] when $y=y_o/2$ yields $IC_{50}$.

Using this assay, the $IC_{50}$ of various compounds are determined. The $IC_{50}$ of various preferred compounds of formula (I) against MMP-7 is about 100 $\mu M$, whereas the $IC_{50}$ of these same compounds against zinc-containing PDF ranged from about 0.004 $\mu M$ to about 0.585 $\mu M$, and against nickel-containing PDF ranged from about 0.001 $\mu M$ to about 0.006 $\mu M$. Accordingly, it can be seen that the compounds provided by the invention have superior selectivity for PDF as compared to their activity against MMP-7. Similar selectivity of the compounds for PDF over MMP-1, MMP-2, MMP-3, MMP-9, MMP-13, MT-MMP-1 and tissue necrosis factor converting enzyme is observed. Similar selectivity is also observed over other metalloproteinases such as angiotensin converting enzyme.

D. Mouse Septicemia Model for Determining in vivo Efficacy

CD1 female out-bred mice (Charles River Laboratories) weighing 18–22 g each are injected intraperitoneally with 0.5 mL of a suspension containing $5\times10^7$ cfu of *S. aureus* (Smith strain) in 7% hog gastric mucosa (mucin). The mice are treated either s.c., i.v. or p.o., 1 hour and 5 hours after infection. Six groups of six mice each are given different dosage levels representing two-fold dilutions of each compound (range of 100–0.1 mg/kg). Vancomycin is used as the control antibiotic and is administered s.c. Compounds are formulated in PBS and untreated controls are dosed with vehicle alone.

Deaths in each group are monitored daily for 6 days and cumulative mortality is used to determine $PD_{50}$, which are calculated using the method of Reed and Muench. The $ED_{50}$ (s.c.) in mice against *S. aureus* for several preferred compound of formula (I) ranged from about 3.45 mg/kg to greater than 10 mg/kg. The $PD_{50}$ (p.o.) in mice against *S. aureus* for these same compounds of formula (I) ranged from 7.06 mg/kg to about 10.83 mg/kg.

E. Pharmacokinetics Study of PDF inhibitors in Mice

The pharmacokinetics of PDF compounds are determined in CD1 female out-bred mice (Charles River Laboratories) weighing 20–25 g. PDF compounds are formulated in 20% cyclodextrin (Aldrich) and filtered through 0.22 µM filter for sterilization. Either single compound or mixtures of 4–6 compounds as a cassette are administered i.v. and p.o. at 10 mL/kg. The dose ranged from 3–15 mg/kg for each compound. At 0.083, 0.25, 0.5, 1, 2, 4 and 7 hours after dosing, serum samples are collected via cardiac puncture under anesthesia. Groups of four mice are used for each time point. The serum samples are stored at −80° C. until analysis.

The serum protein is precipitated by addition of acetonitrile. The samples after protein precipitation are analyzed by LC/MS/MS method. Standard curve is obtained for each compound and used for determination of compound concentration in serum. The pharmacokinetics parameters including $T_{max}$, $C_{max}$, $t_{1/2}$ and AUC, are calculated according to standard method. The oral bioavailability is calculated as the ratio of AUC of p.o. administration versus the AUC administered i.v. The preferred compounds of formula (I) exhibited oral bioavailability greater than 35%.

The compounds of the present invention are, therefore, useful to inhibit bacteria or for the treatment and/or prevention of infectious disorders caused by a variety of bacterial or prokaryotic organisms. Examples include, but are not limited to, Gram positive and Gram negative aerobic and anaerobic bacteria including *Staphylococci*, e.g., *S. aureus* and *S. epidermidis; Enterococci*, e.g., *E. faecalis* and *E. faecium; Streptococci*, e.g., *S. pneumoniae; Haemophilus*, e.g., *H. influenza; Moraxella*, e.g., *M. catarrhalis; Bacteroides*, e.g., *Bacteroides fragilis, Clostridium*, e.g., *Clostridium difficile, Niesseria*, e.g., *N. meningitidis* and *N. gonorrhoae, Legionella* and *Escherichia*, e.g., *E. coli*. Other examples include *Mycobacteria*, e.g., *M. tuberculosis;* intracellular microbes, e.g., *Chlamydia* and *Rickettsiae;* and *Mycoplasma*, e.g., *M. pneumoniae; Pseudomonas*, e.g., *P. aeruginosa; Helicobacter pylori;* and parasites, e.g., *Plasmodium falciparum*.

As used herein, an "infectious disorder" is any disorder characterized by the presence of a microbial infection, such as the presence of bacteria. Such infectious disorders include, for example, central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, antibacterial prophylaxis in immunosuppressed patients, such as patients receiving cancer chemotherapy, or organ transplant patients and chronic diseases caused by infectious organisms, e.g., arteriosclerosis.

The compounds may be used to treat a subject to treat, prevent, and/or reduce the severity of an infection. Subjects include animals, plants, blood products, cultures and surfaces such as those of medical or research equipment, such as glass, needles, surgical equipment and tubing, and objects intended for temporary or permanent implantation into an organism. Preferred animals include mammals, e.g., mice, rats, cats, dogs, cows, sheep, pigs, horses, swine, primates, such as rhesus monkeys, chimpanzees, gorillas and most preferably humans. Treating a subject includes, but is not limited to, preventing, reducing and/or eliminating the clinical symptoms caused by an infection of a subject by a microorganism; preventing, reducing and/or eliminating an infection of a subject by a microorganism; or preventing, reducing and/or eliminating contamination of a subject by a microorganism. The microorganism involved is preferably a prokaryote, more preferably a bacterium.

For the above uses the required dosage will of course vary depending on the mode of administration, the particular condition to be treated and the effect desired. The compositions may contain, for example, from about 0.1% by weight to about 99% by weight, e.g., from about 10–60% by weight, of the active material, depending on the method of administration. Where the compositions comprise dosage units, each unit will contain, for example, from about 1–1000 mg, e.g., 1–500 mg of the active ingredient. The dosage as employed for adult human treatment will range, for example, from about 1–3000 mg/day, for instance, 1500 mg/day depending on the route and frequency of administration. Such a dosage corresponds to about 0.015–50 mg/kg/day. Suitably the dosage is, for example, from about 5–20 mg/kg/day. Suitable unit dosage forms for oral administration comprise ca. 0.25–1500 mg active ingredient.

A "pharmaceutically acceptable carrier" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable carrier" as used in the specification and claims includes both one and more than one such carriers.

The compounds may be administered by any conventional route, e.g., locally or systemically e.g., orally, topically, parenterally, subdermally or by inhalation and may be used for the treatment of bacterial infection in a subject such as animals, preferably, mammals, more preferably, humans.

The compositions may be administered by any conventional route known in the art, e.g., subdermally, by inhalation, orally, topically or parenterally, and may be used for the treatment of bacterial infection in a subject, such as animals, preferably, mammals, more preferably, humans.

The compounds of the invention may be formulated for administration in any convenient way for use in human or veterinary medicine, by analogy with other antibiotics. Such methods are known in the art (see, e.g., Remington's Pharmaceutical Sciences, Easton, Pa.: Mack Publishing Co.) and are not described in detail herein.

The compositions may be in any form known in the art, including but not limited to tablets, capsules, powders, granules, lozenges, creams or liquid preparations, such as oral or sterile parenteral solutions or suspensions. The compounds may also be administered in liposome formulations. The compounds may also be administered as prodrugs, where the prodrug administered undergoes biotransformation in the treated mammal to a form which is biologically active.

The topical formulations of the present invention may be presented as, for instance, ointments, creams or lotions, solutions, salves, emulsions, plasters, eye ointments and eye or ear drops, impregnated dressings and aerosols and may contain appropriate conventional additives, such as preservatives, solvents to assist drug penetration and emollients in ointments and creams.

The formulations may also contain compatible conventional carriers, such as cream or ointment bases and ethanol or oleyl alcohol for lotions. Such carriers may be present, for example, from about 1% up to about 99% of the formulation. For example, they may form up to about 80% of the formulation.

Tablets and capsules for oral administration may be in unit dose presentation form, and may contain conventional excipients, such as binding agents, for example, syrup, acacia, gelatin, sorbitol, tragacanth or polyvinylpyrrollidone; fillers, for example, lactose, sugar, maize-starch, calcium phosphate, sorbitol or glycine; tabletting lubricants, for example, magnesium stearate, talc, polyethylene glycol or silica; disintegrants, for example, potato starch; or acceptable wetting agents, such as sodium lauryl sulphate. The tablets may be coated according to methods well-known in standard pharmaceutical practice.

Oral liquid preparations may be in the form of, for example, aqueous or oily suspensions, solutions, emulsions, syrups or elixirs or may be presented as a dry product for reconstitution with water or another suitable vehicle before use. Such liquid preparations may contain conventional additives, such as suspending agents, for example, sorbitol, methyl cellulose, glucose syrup, gelatin, hydroxyethyl cellulose, carboxymethyl cellulose, aluminium stearate gel or hydrogenated edible fats; emulsifying agents, for example, lecithin, sorbitan monooleate, or acacia; non-aqueous vehicles (which may include edible oils), for example, almond oil, oily esters, such as glycerine, propylene glycol, or ethyl alcohol; preservatives, for example, methyl or propyl p-hydroxybenzoate or sorbic acid, and, if desired, conventional flavoring or coloring agents.

For parenteral administration, fluid unit dosage forms are prepared utilizing the compound and a sterile vehicle, water being preferred. The compound, depending on the vehicle and concentration used, may be either suspended or dissolved in the vehicle or other suitable solvent. In preparing solutions, the compound may be dissolved in water for injection and filter sterilized before filling into a suitable vial or ampoule and sealing. Advantageously, agents such as a local anesthetic preservative and buffering agents may be dissolved in the vehicle. To enhance the stability, the composition may be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization can be accomplished by filtration. The compound may be sterilized by exposure to ethylene oxide before suspending in the sterile vehicle. Advantageously, a surfactant or wetting agent is included in the composition to facilitate uniform distribution of the compound.

The compounds of the invention, e.g., the compounds of formula (I), may be administered in free form or in pharmaceutically acceptable salt form, e.g., as indicated above. Such salts may be prepared in conventional manner and exhibit the same order of activity as the free compounds.

In accordance with the foregoing the present invention further provides:

1.1. A method for treating and/or preventing an infectious disorder in a subject, such as a human or other animal subject, comprising administering to the subject an effective amount of a compound of the invention, e.g., of formula (I), a pharmaceutically acceptable salt thereof or a prodrug thereof.

1.2. A method for inhibiting PDF in a subject comprising administering to the subject an effective PDF inhibiting amount of a compound of the invention, e.g., of formula (I), a pharmaceutically acceptable salt thereof or a prodrug thereof.

2. A compound of the invention, e.g., of formula (I), in free form or in a pharmaceutically acceptable salt form for use as a pharmaceutical, e.g., in any method as indicated under 1.1 or 1.2 above.

3. A pharmaceutical composition, e.g. for use in any of the methods as in 1.1 or 1.2 above comprising a compound of the invention, e.g., of formula (I), in free form or pharmaceutically acceptable salt form, e.g., in association with a pharmaceutically acceptable diluent or carrier therefor.

4. A compound of the invention, e.g., of formula (I), a pharmaceutically acceptable salt or a prodrug thereof for use as a pharmaceutical or in the preparation of a pharmaceutical composition for use in any method as indicated under 1.1 or 1.2 above.

"Treating" or "treatment" of a disease includes:

(a) preventing the disease, i.e., causing the clinical symptoms of the disease not to develop in a subject, e.g., a mammal, that may be exposed to or predisposed to the disease but does not yet experience or display symptoms of the disease;

(b) inhibiting the disease, i.e., arresting or reducing the development of the disease or its clinical symptoms; or (c) relieving the disease, i.e. causing regression of the disease or its clinical symptoms.

An "effective PDF inhibiting amount" means the amount of a compound, a pharmaceutically acceptable salt thereof or a prodrug thereof, that when administered to a subject for treating an infectious disorder responsive to inhibition of PDF or for inhibiting PDF, is sufficient to inhibit PDF. The "effective PDF inhibiting amount" will vary depending on the compound, salt thereof or prodrug thereof, employed, the microorganism that is inhibited in the subject, the age, weight, sex, medical condition, species, disorder and its severity, of the subject to be treated, and the route of administration, but may nevertheless be readily determined by one skilled in the art.

The compounds of the invention, e.g., of formula (I), a pharmaceutically acceptable salt thereof or prodrug thereof, may be administered alone or in combination with another therapeutic agent. Examples of such therapeutic agents include, but are not limited to, other antibacterial agents, such as β-lactams, e.g., penicillins; cephalosporins; carbapenems; ketolides; quinolones, e.g., fluoroquinolones; macrolides, e.g., clarithromycin, azithromycin or vancomycin; rifamycins; monobactams; isoniazid; licosamides; mupirocin; sulfonamides; phenicols; fosfomycin; glycopeptides; tetracyclines; streptogramins; chloramphenicol; and oxazolidinone, anti-inflammatory agents, e.g., corticosteroids or NSAID, analgesics, e.g., narcotic or non-opioic analgesics.

In accordance with the foregoing the present invention provides in a yet further aspect:

5. A method as defined above comprising co-administration, e.g., concomitantly or in sequence, of a therapeutically effective amount of a compound of the invention, e.g., of formula (I), a pharmaceutically acceptable salt thereof or a prodrug thereof, and a second drug substance.

6. A therapeutic combination, e.g., a kit, comprising: a) a compound of the invention, e.g., of formula (I), a pharmaceutically acceptable salt thereof or a prodrug thereof; and b) at least one second active agent. Component a) and component b) may be used concomitantly or in sequence. The kit may comprise instructions for its administration.

The following are representative pharmaceutical formulations containing a compound of the invention.

EXAMPLE A

Tablet Formulation

The following ingredients are mixed intimately and pressed into single scored tablets.

| Ingredient | Quantity per tablet (mg) |
| --- | --- |
| Compound of this invention | 400 |
| Corn starch | 50 |
| Croscarmellose sodium | 25 |
| Lactose | 120 |
| Magnesium stearate | 5 |

EXAMPLE B

Capsule Formulation

The following ingredients are mixed intimately and loaded into a hard-shell gelatin capsule.

| Ingredient | Quantity per capsule (mg) |
| --- | --- |
| Compound of this invention | 200 |
| Lactose, spray-dried | 148 |
| Magnesium stearate | 2 |

EXAMPLE C

Suspension Formulation

The following ingredients are mixed to form a suspension for oral administration.

| Ingredient | | Amount |
| --- | --- | --- |
| Compound of this invention | | 1.0 g |
| Fumaric acid | | 0.5 g |
| Sodium chloride | | 2.0 g |
| Methyl paraben | | 0.15 g |
| Propyl paraben | | 0.05 g |
| Granulated sugar | | 25.0 g |
| Sorbitol (70% solution) | | 13.00 g |
| Veegum K (Vanderbilt Co.) | | 1.0 g |
| Flavoring | | 0.035 mL |
| Colorings | | 0.5 mg |
| Distilled water | q.s. to | 100 mL |

EXAMPLE D

Injectable Formulation

The following ingredients are mixed to form an injectable formulation.

| Ingredient | Amount |
| --- | --- |
| Compound of this invention | 0.2–20 mg |
| Sodium acetate buffer solution, 0.4 M | 2.0 mL |
| HCl (1 N) or NaOH (1 N) | q.s. to suitable pH |
| Water (distilled, sterile) | q.s. to 20 mL |

EXAMPLE E

Suppository Formulation

A suppository of total weight 2.5 g is prepared by mixing the compound of the invention with Witepsol® H-15 (triglycerides of saturated vegetable fatty acid; Riches-Nelson, Inc., N.Y.), and has the following composition:

| Compound of the invention | 500 mg |
| --- | --- |
| Witepsol ® H-15 | balance |

The present invention is not limited to the clinical use of the compounds of the invention, i.e, in the treatment of infection in a subject. The compounds of the invention are useful to inhibit bacteria wherever it is desired to inhibit bacteria by contacting the bacteria with one or more compounds of the invention. Because of their ability to inhibit bacteria, the compounds of the invention are particularly useful to prevent contamination of cell cultures. As used in this context, the term "inhibit" means the suppression, control, stasis, or kill of bacteria. Eukaryotic cells, in particular animal cells, are often cultured for various reasons such as for their ability to produce substances such as proteins. Examples of such cells include Chinese hamster ovary cells (CHO cells), African green monkey kidney cells, hybridomoas constructed by fusing a parent cell (myeloma, etc.) with a useful substance-producing normal cell (lymphocyte, etc.), and the like. Typically, the compounds of the invention are incorporated into cell culture media at a bacteria inhibiting amount, e.g., a concentration of about 0.0001 mg/mL to about 10 mg/mL, preferably about 0.0001 mg/mL to about 1 mg/mL, and more preferably about 0.001 mg/mL to about 0.1 mg/mL. Any conventional cell culture medium known in the art can be used.

In accordance with the foregoing the present invention provides in a yet further aspect:

7. A method for preventing bacterial contamination of a cell culture medium comprising incorporating into said cell culture medium a bacteria inhibiting amount of a compound of the invention, e.g., of formula (I), or a pharmaceutically acceptable salt thereof.

8. A cell culture medium comprising. a bacteria inhibiting amount of a compound of the invention, e.g., of formula (I), or a pharmaceutically acceptable salt thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. An N-[1-oxo-(optionally 2-aza)-2-alkyl-3-(carboxyl or thiol or hydroxyaminocarbonyl or N-hydroxyformamido)-propyl]-(aryl or heteroaryl)-azacyclo$_{4-7}$alkane or thiazacyclo$_{4-7}$alkane, a pharmaceutically acceptable salt thereof, or a prodrug thereof.

2. A compound according to claim 1 of formula (I):

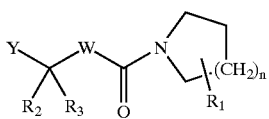

wherein:
$R_1$ is an aryl or heteroaryl which is linked to either the α-or β-position to the ring nitrogen;
$R_2$ is hydrogen, halogen or hydroxy;
$R_3$ is hydrogen, halogen, $C_{1-10}$ alkyl, $C_{1-10}$ heteroalkyl or ($R_2$ and $R_3$) collectively form a $C_{4-7}$ cycloalkyl, provided that when $R_3$ is halogen, $R_2$ is not hydroxy;
X is —CH$_2$—;
W is NR$_5$ or CR$_4$R$_5$, wherein $R_4$ is hydrogen, halogen, $C_{1-10}$ alkyl, or $C_{1-10}$ heteroalkyl and $R_5$ is $C_{1-10}$ alkyl or ($R_4$ and $R_5$) collectively form a $C_{4-7}$ cycloalkyl, provided that when W is NR$_5$, $R_2$ and $R_3$ are hydrogen, $C_{1-10}$ alkyl or heteroalkyl;
Y is —COOH, —SH, —N(OH)—CHO or —CO—NH (OH), provided that when Y is —N(OH)CHO or —SH, $R_2$ is hydrogen and $R_3$ is hydrogen, $C_{1-10}$ alkyl or $C_{1-10}$ heteroalkyl;
n is 1;
a pharmaceutically acceptable salt thereof or a prodrug thereof.

3. The compound of formula (I) according to claim 2, wherein Y is —CO—NH(OH).

4. The compound of formula (I) according to claim 2, wherein X is —CH$_2$—, $R_3$ and $R_4$ are hydrogen, $R_5$ is lower alkyl and n is 1.

5. The compound of formula (I) according to claim 2, wherein $R_1$ is hydroxy.

6. The compound of formula (I) according to claim 2, wherein $R_5$ is n-butyl.

7. The compound of formula (I) according to claim 2, wherein $R_1$ is heteroaryl.

8. The compound of formula (I) according to claim 2, wherein the heteroaryl is oxazolyl, thiazolyl, pyridinyl and benzimidazolyl.

9. The compound of formula (I) according to claim 2, wherein the heteroaryl is linked to the α-position to the nitrogen of the azacycloalkane represented in formula (I).

10. The compound of formula (I) according to claim 2, wherein the heteroaryl is oxazolyl.

11. The compound of formula (I) according to claim 2, wherein oxazolyl is substituted by one or two lower alkyl.

12. The compound of formula (I) according to claim 2, wherein the heteroaryl is thiazolyl.

13. The compound of formula (I) according to claim 12, wherein the thiazolyl is substituted by one or two substituents selected from the group consisting of lower alkyl and phenyl.

14. The compound of formula (I) according to claim 2, wherein the heteroaryl is pyridinyl.

15. The compound of formula (I) according to claim 2, wherein the heteroaryl is benzimidazolyl.

16. The compound of formula (I) according to claim 2, wherein $R_2$ is hydrogen and W is N.

17. The compound of formula (I) according to claim 16, wherein $R_5$ is a substituted lower alkyl.

18. The compound of formula (I) according to claim 16, wherein $R_1$ is a heteroaryl.

19. The compound of formula (I) according to claim 16, wherein the heteroaryl is oxazolyl and thiaazolyl.

20. The compound of formula (I) according to claim 16, wherein the heteroaryl is linked to the α-position of the azacycloalkane represented in formula (I).

21. The compound of formula (I) according to claim 16, wherein the heteroaryl is oxazolyl.

22. The compound of formula (I) according to claim 16, wherein the heteroaryl is thiazolyl.

23. The compound of formula (I) according to claim 22, wherein the thiazolyl is substituted with phenyl.

24. The compound of formula (I) according to claim 2, wherein $R_1$ is an aryl.

25. The compound of formula (I) according to claim 24, wherein the aryl is a phenyl.

26. The compound of formula (I) according to claim 2, wherein $R_1$ is halogen.

27. The compound of formula (I) according to claim 26, wherein the halogen is fluorine.

28. The compound of formula (I) according to claim 2, wherein X is —N(OH)—CHO.

29. The compound of formula (I) according to claim 28, wherein X is —CH$_2$—, W is carbon, n is 1, $R_2$, $R_3$, $R_4$ are independently H or lower alkyl, and $R_5$ is lower alkyl.

30. The compound of formula (I) according to claim 28, wherein $R_2$, $R_3$ and $R_4$ are each hydrogen.

31. The compound of formula (I) according to claim 28, wherein $R_1$ is a heteroaryl.

32. The compound of formula (I) according to claim 28, wherein the heteroaryl is oxazolyl or pyridinyl.

33. The compound of formula (I) according to claim 28, wherein the heteroaryl is linked at the α-position of the azacycloalkane represented in formula (I).

34. The compound of formula (I) according to claim 2 wherein the compound is selected from the group consisting of 2(S)-hydroxy-3(R)-[2(S)-oxazol-2-yl-pyrrolidine-1-carbonyl)-heptanoic acid hydroxamide, N-hydroxy-N-[2-(2-oxazol-2-yl-pyrrolidine-1-carbonyl)-hexyl]-formamide, 2(S)-hydroxy-3 (R)-[2(S)-(5 -methyl-oxazol-2-yl-pyrrolidine-1-carbonyl)-heptanoic acid hydroxamide, and 2(S)-fluoro-3-(R)-[2-S-(5-methyloxazol-2-yl-pyrrolidine-1-carbonyl)-heptanoic acid hydroxamide.

35. A pharmaceutical composition comprising a compound according to claim 1 and a pharmaceutically acceptable carrier.

36. A method for inhibiting bacteria comprising contacting said bacteria with a bacteria inhibiting amount of a compound according to claim 1 or a pharmaceutically acceptable salt thereof.

* * * * *